(12) United States Patent
Kamali-Zare et al.

(10) Patent No.: US 10,573,414 B2
(45) Date of Patent: Feb. 25, 2020

(54) METHODS AND SYSTEMS FOR IDENTIFYING BRAIN DISORDERS

(71) Applicant: DARMIYAN, INC., Emeryville, CA (US)

(72) Inventors: Padideh Kamali-Zare, Emeryville, CA (US); Kaveh Vejdani, Emeryville, CA (US); Thomas Liebmann, Emeryville, CA (US); Hesaam Esfandyarpour, Emeryville, CA (US)

(73) Assignee: DARMIYAN, INC., Emeryville, CA (US)

( * ) Notice: Subject to any disclaimer, the term of this patent is extended or adjusted under 35 U.S.C. 154(b) by 2 days.

(21) Appl. No.: 15/987,794

(22) Filed: May 23, 2018

(65) Prior Publication Data

US 2018/0268942 A1  Sep. 20, 2018

Related U.S. Application Data

(63) Continuation of application No. PCT/US2017/064745, filed on Dec. 5, 2017.

(Continued)

(51) Int. Cl.
*A61B 5/055* (2006.01)
*G16H 50/50* (2018.01)
(Continued)

(52) U.S. Cl.
CPC .......... *G16H 50/50* (2018.01); *A61B 5/0042* (2013.01); *A61B 5/055* (2013.01); *A61B 5/4082* (2013.01);
(Continued)

(58) Field of Classification Search
CPC ........ G16H 50/50; G16H 50/70; G16H 30/40; A61B 5/4094; A61B 5/0042;
(Continued)

(56) References Cited

U.S. PATENT DOCUMENTS

2008/0170791 A1* 7/2008 Eskildsen ................. G06K 9/48
 382/199
2010/0241020 A1* 9/2010 Zaidel ................. A61B 5/04001
 600/544

(Continued)

FOREIGN PATENT DOCUMENTS

WO  WO-2018106713 A1  6/2018

OTHER PUBLICATIONS

2016 Alzheimer's disease facts and figures. Alzheimers Dement 12(4):459-509 (2016).

(Continued)

*Primary Examiner* — Jonathan Cwern
(74) *Attorney, Agent, or Firm* — Wilson Sonsini Goodrich & Rosati

(57) ABSTRACT

Methods and systems for determining whether brain tissue is indicative of a disorder, such as a neurodegenerative disorder, are provided. The methods and systems generally utilize data processing techniques to assess a level of congruence between measured parameters obtained from magnetic resonance imaging (MRI) data and simulated parameters obtained from computational modeling of brain tissues.

30 Claims, 20 Drawing Sheets

Related U.S. Application Data

(60) Provisional application No. 62/481,839, filed on Apr. 5, 2017, provisional application No. 62/430,351, filed on Dec. 6, 2016.

(51) Int. Cl.

| | |
|---|---|
| *G16H 50/70* | (2018.01) |
| *G16H 30/40* | (2018.01) |
| *A61B 5/00* | (2006.01) |
| *G06T 7/00* | (2017.01) |
| *G06T 17/10* | (2006.01) |

(52) U.S. Cl.
CPC .......... *A61B 5/4088* (2013.01); *A61B 5/4094* (2013.01); *A61B 5/7278* (2013.01); *G06T 7/0016* (2013.01); *G06T 17/10* (2013.01); *G16H 30/40* (2018.01); *G16H 50/70* (2018.01); *G06T 2207/10088* (2013.01); *G06T 2207/30016* (2013.01)

(58) Field of Classification Search
CPC ... A61B 5/4082; A61B 5/4088; A61B 5/7278; A61B 5/055; G06T 7/0016; G06T 17/10; G06T 2207/30016; G06T 2207/10088
USPC .......................................................... 600/416
See application file for complete search history.

(56) References Cited

U.S. PATENT DOCUMENTS

| | | | |
|---|---|---|---|
| 2010/0259263 A1* | 10/2010 | Holland .................. | A61B 5/055 324/310 |
| 2015/0073258 A1* | 3/2015 | Mazer ..................... | G01R 33/50 600/410 |
| 2016/0239969 A1* | 8/2016 | Davatzikos ........... | G06T 7/0014 |

OTHER PUBLICATIONS

Augustinack et al. Entorhinal verrucae geometry is coincident and correlates with Alzheimer's lesions: a combined neuropathology and high-resolution ex vivo MRI analysis. Acta Neuropathol 123(1):85-96 (2012).
Bakker et al. Lymphatic Clearance of the Brain: Perivascular, Paravascular and Significance for Neurodegenerative Diseases. Cell Mol Neurobiol 36(2):181-194 (2016).
Barnett et al. Early intervention in Alzheimer's disease: a health economic study of the effects of diagnostic timing. BMC Neurology 14:101 (2014).
Cash et al. The pattern of atrophy in familial Alzheimer disease: volumetric MRI results from the DIAN study. Neurology 81(16):1425-1433 (2013).
Cavedo et al. The Road Ahead to Cure Alzheimer's Disease: Development of Biological Markers and Neuroimaging Methods for Prevention Trials Across all Stages and Target Populations. J Prev Alzheimers Dis 1(3):181-202 (2014).
Chen et al. Detecting microstructural properties of white matter based on compartmentalization of magnetic susceptibility. NeuroImage 70:1-9 (2013).
Fischer et al. Conversion from subtypes of mild cognitive impairment to Alzheimer dementia. Neurology 68(4):288-291 (2007).
Friedman et al. US Prevalence And Predictors Of Informal Caregiving For Dementia. Health Aff (Millwood) 34(10):1637-1641 (2015).
Gauthier et al. Mild cognitive impairment. Lancet 367(9518):1262-70 (2006).
Greene et al. Subregions of the inferior parietal lobule are affected in the progression to Alzheimer's disease. Neurobiol Aging 31(8):1304-1311 (2010).
Hampel et al. Core candidate neurochemical and imaging biomarkers of Alzheimer's disease. Alzheimers Dement 2008. 4(1):38-48.
Hebert et al. Alzheimer disease in the United States (2010-2050) estimated using the 2010 census. Neurology 80(19):1778-1783 (2013).
Hebert et al. Annual incidence of Alzheimer disease in the United States projected to the years 2000 through 2050. Alzheimer Dis Assoc Disord 15:169-173 (2001).
Hrabetova et al. Dead-space microdomains hinder extracellular diffusion in rat neocortex during ischemia. J Neurosci 23(23):8351-8359 (2003).
Huang et al. Longitudinal measurement and hierarchical classification framework for the prediction of Alzheimer's disease. Sci Rep 7:39880 (2017).
Jenkins et al. Developmental and age-related changes in rat brain glycosaminoglycans. J Neurochem 51(5):1634-1640 (1988).
Kamali-Zare et al. Brain extracellular space: geometry, matrix and physiological importance. Basic Clin Neurosci 4(4):282-286 (2013).
Kloppel et al. Diagnostic neuroimaging across diseases. NeuroImage 61:457-463 (2012).
Kruggel et al. Analysis of longitudinal diffusion-weighted images in healthy and pathological aging: An ADNI study. J Neurosci Methods 278:101-115 (2017).
Lerch et al. Studying neuroanatomy using MRI. Nat Neurosci 20(3):314-326 (2017).
Liebmann et al. Three-Dimensional Study of Alzheimer's Disease Hallmarks Using the iDISCO Clearing Method. Cell Rep 16(4):1138-1152 (2016).
Mayo et al. Longitudinal changes in microstructural white matter metrics in Alzheimer's disease. Neuroimage Clin 13:330-338 (2017).
Nicholson et al. Brain Extracellular Space as a Diffusion Barrier. Comput Vis Sci 14(7):309-325 (2011).
Nicholson et al. Diffusion of molecules in brain extracellular space: theory and experiment. Prog Brain Res 125:129-154 (2000).
Nicholson et al. Extracellular space structure revealed by diffusion analysis. Trends Neurosci 21(5):207-215 (1998).
Nicholson et al. Hindered diffusion of high molecular weight compounds in brain extracellular microenvironment measured with integrative optical imaging. Biophys J 65(6):2277-2290 (1993).
Paus. Inferring causality in brain images: a perturbation approach. Phil Trans R. Soc. B. 360:1109-1114 (2005).
PCT/US2017/064745 International Search Report and Written Opinion dated Feb. 21, 2018.
Petersen et al. Mild cognitive impairment: clinical characterization and outcome. Arch Neurol 56(3):303-308 (1999).
Ruan et al. Potential neuroimaging biomarkers of pathologic brain changes in Mild Cognitive Impairment and Alzheimer's disease: a systematic review. BMC Geriatr 16:104 (2016).
Schmand et al. Meta-analysis of CSF and MRI biomarkers for detecting preclinical Alzheimer's disease. Psychol Med 40(1):135-145 (2010).
Sykova et al. Changes in extracellular space size and geometry in APP23 transgenic mice: a model of Alzheimer's disease. PNAS USA 102(2):479-484 (2005).
Sykova et al. Diffusion in brain extracellular space. Physiol Rev 88(4):1277-1340 (2008).
Tao et al. Maximum geometrical hindrance to diffusion in brain extracellular space surrounding uniformly spaced convex cells. J Theor Biol 229(1):59-68 (2004).
Thomann et al. The cerebellum in mild cognitive impairment and Alzheimer's disease—a structural MRI study. J Psychiatr Res 42(14):1198-1202 (2008).
Vishnu. Implications of presymptomatic change in thalamus and caudate in Alzheimer's disease. Brain 136(Pt 11):e258 (2013).
Weimer et al. Early identification and treatment of Alzheimer's disease: social and fiscal outcomes. Alzheimers Dement 5:215-226 (2009).
Weiner et al. 2014 Update of the Alzheimer's Disease Neuroimaging Initiative: A review of papers published since its inception. Alzheimers Dement 11(6):e1-120 (2015).
Xie et al. Sleep drives metabolite clearance from the adult brain. Science 342(6156):373-377 (2013).
Yoshiyama et al. Synapse loss and microglial activation precede tangles in a P301S tauopathy mouse model. Neuron 53(3):337-351 (2007).

(56) References Cited

OTHER PUBLICATIONS

Yousefnezhad et al. Unified model of brain tissue microstructure dynamically binds diffusion and osmosis with extracellular space geometry. Phys Rev E 94(3-1):032411 (2016).

* cited by examiner

METHODS AND SYSTEMS FOR IDENTIFYING BRAIN DISORDERS

CROSS-REFERENCE

This application is a continuation of International Application No. PCT/US2017/064745, filed Dec. 5, 2017, which claims the benefit of U.S. Provisional Patent Application Ser. No. 62/430,351, filed Dec. 6, 2016, and U.S. Provisional Patent Application Ser. No. 62/481,839, filed Apr. 5, 2017, each of which is entirely incorporated herein by reference for all purposes.

BACKGROUND

Neurodegenerative diseases leading to dementia are a tremendous societal burden, currently devastating 9 million people domestically and 47 million people worldwide. Current inability to effectively prevent, diagnose and combat neurodegeneration results in staggering direct and indirect costs Alzheimer's disease (AD), the most common cause of dementia, alone afflicts over 5 million Americans and accounts for the 6th leading cause of death in the USA. AD requires an estimated 18 billion hours of unpaid caretaking and well over $250 billion of medical costs annually. Prevalence of the disease is projected to escalate to nearly 14 million people domestically and 135 million worldwide by 2050, with no potential cure in immediate sight. There is a dire need for technological advancements toward diagnostics, prevention, therapeutics and eventual cures that will each have profound beneficial impacts on the population.

Current clinical evaluation typically includes non-invasive brain imaging with magnetic resonance imaging (MRI), positron emission tomography (PET), or other advanced imaging strategies which provide insight into tissue volume changes, chemical composition, cortical metabolic rate, alterations associated with tissue cellularity and disease biomarkers, and structural abnormalities attributed to neurodegenerative disease. To aid in the diagnosis of AD and differential diagnosis from non-Alzheimer dementias, fluorodeoxyglucose (FDG) PET and amyloid PET reveal AD-associated patterns of cerebral cortical metabolism and beta amyloid deposits in the gray matter, respectively. Similarly, tau PET reveals neurofibrillary tangles in the brain. However, due to a lack of advancement in analysis technologies, meaningful use of these imaging techniques for neurodegenerative disease is restricted to late stages when considerable tissue damage and cognitive or other clinical abnormalities are present. As we deepen our understanding of the multiplicity of abnormalities associated with AD, there is increasing evidence that the continual targeting of these amyloid plaques and neurofibrillary tangles may merely be treating late stage symptoms rather than the underlying causes. The inability to effectively detect early stages of AD precludes pre-symptomatic intervention and conceals the potential beneficial effects of drug candidates.

Implicit to the neurodegenerative process is the death of the signaling nerve cells in the brain, though this can merely be the ultimate consequence in a cascade of degeneration within brain tissue. The structural integrity of tissue is necessary for neuron support and survival and clearance of molecular waste that must be removed from the brain for maintenance of neural tissue homeostasis and efficient function. Alterations in non-cellular components of the brain are complicit in the degenerative process and may be a precursor of lost nerve cell function. It has been shown that proper regulation of neural tissue homeostasis is necessary for eliminating toxic residue buildup, a process that can be altered in the AD brain. Yet, there remains limited understanding of brain structural content and its impact on transport of molecules in the brain interstitium. Currently, the clinical use and the diagnostic capacity of brain MRI remains limited to differential diagnosis, only after symptomatic presentation, principally due to the inherently low spatial resolution—MRI image voxels are in mm dimensions, whereas structural changes contributing to tissue degeneration originate at the sub-micron scale. FDG, amyloid, and tau PET scans suffer from similar limitations.

SUMMARY

Recognized herein is a need for tools that allow early detection of Alzheimer's disease and other neurodegenerative disorders, including tools that may utilize approaches that detect microscopic changes in brain tissue from low-resolution magnetic resonance imaging (MRI) scans. Such approaches may leverage a deeper understanding of brain tissue microstructure to more reliably predict and interpret the health of the brain from MRI scans well before severe tissue damage irreversibly impedes healthy cognitive function.

Provided herein is an image analysis platform that can detect and quantify brain tissue abnormality (such as neurodegeneration) in every voxel of standard clinical brain MRI. The platform may provide detailed information about the brain tissue health at the microscopic level and the resulting observed patterns of pathologic involvement that is currently missing in the neuroimaging/brain diagnostics field. As a result, complex brain diseases, such as Alzheimer's disease, which are currently diagnosed very late (i.e., at the late symptomatic stages), may be diagnosed or otherwise identified prior to the onset of advanced symptoms. The platform may allow early-stage testing of novel drug candidates for clinical trials, which have previously failed due to poor patient selection, late intervention, and very high trial costs. All of these factors may be significantly improved using the platform.

Provided herein are methods and systems for determining whether brain tissue is indicative of a disorder, such as a neurodegenerative disorder. The methods and systems may allow the early diagnosis of a brain disorder much earlier than would be possible using prior methods and systems, such as many years before the development of symptoms associated with the disorder that are detectable using prior methods and systems. The methods and systems may provide high accuracy in diagnosing a brain disorder (such as greater than 90% accuracy), as measured by a variety of criteria described herein.

The methods and systems of the present disclosure may utilize data processing techniques to assess a level of congruence between measured parameters obtained from magnetic resonance imaging (MRI) data and simulated parameters obtained from computational modeling of brain tissues. The methods and systems generally operate by determining a level of congruence between the one or more measured parameters and the one or more simulated parameters for one or more voxels of the MRI data. The simulated parameters are obtained from a plurality of microstructural models. Each microstructural model of the plurality of microstructural models is obtained by subjecting a microstructural model that is not indicative of a disorder to a series of microstructural perturbations. After assessing the level of congruence between the one or more measured parameters and the one or more simulated parameters for a number of microstructural models of the plurality of microstructural models, a diagnostic microstructural model that meets a threshold congruence is selected. The diagnostic microstructural model is used to determine the disorder state of the brain tissue associated with the voxel.

The methods and systems may be applied to a plurality of voxels of the MRI data, such that a level of congruence is determined for each voxel of the plurality of voxels. In this manner, a diagnostic model and a disorder state may be determined for each voxel of the plurality of voxels. The methods and systems may be applied to determine a diagnostic model and a disorder state for a plurality of voxels located within a particular region of a brain, within a whole brain, or across a plurality of brains from a plurality of subjects.

In an aspect, a method for determining a disorder state of brain tissue in a brain of a subject may comprise: (a) obtaining magnetic resonance imaging (MRI) data comprising at least one MRI image of the brain, the MRI image comprising a plurality of voxels, a voxel of the plurality of voxels being associated with the brain tissue of the brain of the subject and comprising one or more measured MRI parameters in the MRI data; (b) for the voxel of the plurality of voxels, using one or more computer processors to process the one or more measured MRI parameters with one or more simulated MRI parameters for the voxel, the one or more simulated MRI parameters being generated from one or more microstructural models at the voxel; (c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and (d) for the voxel of the plurality of voxels, using the diagnostic model to determine the disorder state of the brain tissue associated with the voxel.

Each voxel may comprise a plurality of measured MRI parameters. The one or more measured MRI parameters may be a plurality of measured MRI parameters. The one or more simulated MRI parameter may be a plurality of simulated MRI parameters.

The method may further comprise repeating (b)-(d) one or more times for additional voxels of the plurality of voxels. The method may further comprise repeating (b)-(d) for all other voxels of the plurality of voxels. The method may further comprise repeating (b)-(d) for all voxels associated with a specified region of the brain. The method may further comprise repeating (b)-(d) for all voxels associated with an entirety of the brain. The method may further comprise repeating (a)-(d) for a plurality of MRI images, each MRI image of the plurality of MRI images associated with a brain selected from a plurality of brains, each brain of the plurality of brains associated with a subject selected from a plurality of subjects.

The MRI image may be selected from the group consisting of: a longitudinal relaxation time (T1)-weighted MRI image, a transverse relaxation time (T2)-weighted MRI image, and a diffusion-weighted MRI image. The measured MRI parameter may be selected from the group consisting of: a longitudinal relaxation time (T1), a transverse relaxation time (T2), and a diffusion coefficient. The simulated MRI parameter may be selected from the group consisting of: a longitudinal relaxation time (T1), a transverse relaxation time (T2), and a diffusion coefficient.

The one or more microstructural models may comprise information regarding a parameter selected from the group consisting of: intracellular content, extracellular content, distribution of extracellular content within interstitial space, distribution of intracellular content within intracellular space, and tissue geometry. The one or more microstructural models may comprise measured or predicted values of a parameter selected from the group consisting of: cell density, cell shape, cell geometry, cell size, cell distribution, intercellular spacing, extracellular matrix homogeneity, interstitial tortuosity, water to protein ratio, water to lipid ratio, water to carbohydrate ratio, protein to lipid ratio, protein to carbohydrate ratio, and lipid to carbohydrate ratio. The one or more microstructural models may be selected from a microstructural model library. The microstructural model library may comprise at least 100 microstructural models.

The microstructural model library may be constructed by: (a) creating a first microstructural model corresponding to a brain state that is not associated with a disorder; and (b) iteratively subjecting the first microstructural model to a perturbation, each iteration producing an additional perturbed microstructural model. (b) may comprise subjecting the first microstructural model to at least 100 iterations to generate at least 100 perturbed microstructural models. The first microstructural model may be selected based on knowledge of the brain region associated with the voxel. The perturbation may comprise an operation selected from the group consisting of: depleting cells, altering cellular morphology or distribution, altering intracellular or interstitial physico-chemical composition or distribution, altering extracellular matrix composition or distribution, and altering intercellular spacing. The perturbation may comprise a stochastic procedure.

The threshold congruence may be determined by computing an objective function between the one or more measured MRI parameters and the one or more simulated MRI parameters. The objective function may comprise an L1 norm or an L2 norm.

Determining the disorder state of the brain tissue associated with the voxel may be achieved at an accuracy of at least 90%. Determining the disorder state across the brain tissue associated with the specified region of the brain may be achieved at an accuracy of at least 90%. Determining the disorder state of the brain tissue associated with the whole brain of the subject may be achieved at an accuracy of at least 90%. Determining the disorder state of the brain tissue associated with the plurality of subjects may be achieved at an accuracy of at least 90%.

The disorder may be a non-neurodegenerative disorder. The disorder may be selected from the group consisting of: a primary neoplasm, a metastatic neoplasm, a seizure disorder, a seizure disorder with focal cortical dysplasia, a demyelinating disorder, a non-neurodegenerative encephalopathy, a cerebrovascular disease, and a psychological disorder. The disorder may be a neurodegenerative disorder. The disorder may be selected from the group consisting of: Alzheimer's disease, a non-Alzheimer's dementia disorder, Parkinson's disease, a Parkinsonism disorder, a motor neuron disease, Huntington's disease, a Huntington's disease-like syndrome, transmissible spongiform encephalopathy, chronic traumatic encephalopathy, and a tauopathy.

The method may enable diagnosis of a neurodegenerative disorder more than 5 years prior to the development of symptoms associated with the neurodegenerative disorder. The method may enable monitoring of the neurodegenerative disorder at a plurality of time points, the plurality of time points separated by a plurality of time intervals.

The method may further comprise constructing a brain map that, for each voxel of the plurality of voxels, indicates the disorder state of the brain tissue associated with the voxel. The method may further comprise displaying the brain map on a graphical user interface of an electronic device of a user. The brain map may comprise a qualitative abnormality map. The brain map may comprise a binary abnormality map. The brain map may comprise a quantitative abnormality map. The brain map may comprise a percent abnormality map.

In an aspect, a method for determining a disorder state of a tissue in a portion of a body of a subject may comprise: obtaining magnetic resonance imaging (MRI) data comprising at least one MRI image of the tissue, the MRI image comprising a plurality of voxels, a voxel of the plurality of voxels being associated with the tissue of the subject and comprising one or more measured MRI parameters in the MRI data; (b) for the voxel of the plurality of voxels, using one or more computer processors to process the one or more measured MRI parameters with one or more simulated MRI parameters for the voxel, the one or more simulated MRI parameters being generated from one or more microstructural models at the voxel; (c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and (d) for the voxel of the plurality of voxels, using the diagnostic model to determine the disorder state of the tissue associated with the voxel.

The tissue may be selected from the group consisting of: spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, and non-brain tissue of the head and neck.

In an aspect, a non-transitory computer-readable medium may comprise machine-executable code that, upon execution by one or more computer processors, implements a method for detecting a disorder state of brain tissue in a brain of a subject, the method comprising: (a) obtaining magnetic resonance imaging (MRI) data comprising at least one MRI image of the brain, the MRI image comprising a plurality of voxels, a voxel of the plurality of voxels being associated with the brain tissue of the brain of the subject and comprising one or more measured MRI parameters in the MRI data; (b) for the voxel of the plurality of voxels, using one or more computer processors to process the one or more measured MRI parameters with one or more simulated MRI parameters for the voxel, the one or more simulated MRI parameters being generated from one or more microstructural models at the voxel; (c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and (d) for the voxel of the plurality of voxels, using the diagnostic model to determine the disorder state of the brain tissue associated with the voxel.

Each voxel may comprise a plurality of measured MRI parameters. The one or more measured MRI parameters may be a plurality of measured MRI parameters. The one or more simulated MRI parameter may be a plurality of simulated MRI parameters.

The method may further comprise repeating (b)-(d) one or more times for additional voxels of the plurality of voxels. The method may further comprise repeating (b)-(d) for all other voxels of the plurality of voxels. The method may further comprise repeating (b)-(d) for all voxels associated with a specified region of the brain. The method may further comprise repeating (b)-(d) for all voxels associated with an entirety of the brain. The method may further comprise repeating (a)-(d) for a plurality of MRI images, each MRI image of the plurality of MRI images associated with a brain selected from a plurality of brains, each brain of the plurality of brains associated with a subject selected from a plurality of subjects.

The MRI image may be selected from the group consisting of: a longitudinal relaxation time (T1)-weighted MRI image, a transverse relaxation time (T2)-weighted MRI image, and a diffusion-weighted MRI image. The measured MRI parameter may be selected from the group consisting of: a longitudinal relaxation time (T1), a transverse relaxation time (T2), and a diffusion coefficient. The simulated MRI parameter may be selected from the group consisting of: a longitudinal relaxation time (T1), a transverse relaxation time (T2), and a diffusion coefficient.

The one or more microstructural models may comprise information regarding a parameter selected from the group consisting of: intracellular content, extracellular content, distribution of extracellular content within interstitial space, distribution of intracellular content within intracellular space, and tissue geometry. The one or more microstructural models may comprise measured or predicted values of a parameter selected from the group consisting of: cell density, cell shape, cell geometry, cell size, cell distribution, intercellular spacing, extracellular matrix homogeneity, interstitial tortuosity, water to protein ratio, water to lipid ratio, water to carbohydrate ratio, protein to lipid ratio, protein to carbohydrate ratio, and lipid to carbohydrate ratio. The one or more microstructural models may be selected from a microstructural model library. The microstructural model library may comprise at least 100 microstructural models.

The microstructural model library may be constructed by: (a) creating a first microstructural model corresponding to a brain state that is not associated with a disorder; and (b) iteratively subjecting the first microstructural model to a perturbation, each iteration producing an additional perturbed microstructural model. (b) may comprise subjecting the first microstructural model to at least 100 iterations to generate at least 100 perturbed microstructural models. The first microstructural model may be selected based on knowledge of the brain region associated with the voxel. The perturbation may comprise an operation selected from the group consisting of: depleting cells, altering cellular morphology or distribution, altering intracellular or interstitial physico-chemical composition or distribution, altering extracellular matrix composition or distribution, and altering intercellular spacing. The perturbation may comprise a stochastic procedure.

The threshold congruence may be determined by computing an objective function between the one or more measured MRI parameters and the one or more simulated MRI parameters. The objective function may comprise an L1 norm or an L2 norm.

Determining the disorder state of the brain tissue associated with the voxel may be achieved at an accuracy of at least 90%. Determining the disorder state across the brain tissue associated with the specified region of the brain may be achieved at an accuracy of at least 90%. Determining the disorder state of the brain tissue associated with the whole brain of the subject may be achieved at an accuracy of at least 90%. Determining the disorder state of the brain tissue associated the plurality of subjects may be achieved at an accuracy of at least 90%.

The disorder may be a non-neurodegenerative disorder. The disorder may be selected from the group consisting of: a primary neoplasm, a metastatic neoplasm, a seizure disorder, a seizure disorder with focal cortical dysplasia, a demyelinating disorder, a non-neurodegenerative encephalopathy, a cerebrovascular disease, and a psychological disorder. The disorder may be a neurodegenerative disorder. The disorder may be selected from the group consisting of: Alzheimer's disease, a non-Alzheimer's dementia disorder, Parkinson's disease, a Parkinsonism disorder, a motor neuron disease, Huntington's disease, a Huntington's disease-like syndrome, transmissible spongiform encephalopathy, chronic traumatic encephalopathy, and a tauopathy.

The method may enable diagnosis of a neurodegenerative disorder more than 5 years prior to the development of symptoms associated with the neurodegenerative disorder. The method may enable monitoring of the neurodegenerative disorder at a plurality of time points, the plurality of time points separated by a plurality of time intervals.

The method may further comprise constructing a brain map that, for each voxel of the plurality of voxels, indicates the disorder state of the brain tissue associated with the voxel. The method may further comprise displaying the brain map on a graphical user interface of an electronic device of a user. The brain map may comprise a qualitative abnormality map. The brain map may comprise a binary abnormality map. The brain map may comprise a quantitative abnormality map. The brain map may comprise a percent abnormality map.

In an aspect, a non-transitory computer-readable medium may comprise machine-executable code that, upon execution by one or more computer processors, implements a method for detecting a disorder state of brain tissue in a brain of a subject, the method comprising: obtaining magnetic resonance imaging (MRI) data comprising at least one MRI image of the tissue, the MRI image comprising a plurality of voxels, a voxel of the plurality of voxels being associated with the tissue of the subject and comprising one or more measured MRI parameters in the MRI data; (b) for the voxel of the plurality of voxels, using one or more computer processors to process the one or more measured MRI parameters with one or more simulated MRI parameters for the voxel, the one or more simulated MRI parameters being generated from one or more microstructural models at the voxel; (c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and (d) for the voxel of the plurality of voxels, using the diagnostic model to determine the disorder state of the tissue associated with the voxel.

The tissue may be selected from the group consisting of: spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, and non-brain tissue of the head and neck.

In an aspect, a system for determining a disorder state of brain tissue in a brain of a subject may comprise: (a) a database comprising magnetic resonance imaging (MRI) data comprising at least one MRI image of the brain, the MRI image comprising a plurality of voxels, a voxel of the plurality of voxels being associated with the brain tissue of the brain of the subject and comprising a measured MRI parameter in the MRI data; and (b) one or more computer processors operatively coupled to the database, wherein the one or more computer processors are individually or collectively programmed to: (i) for the voxel of the plurality of voxels, use one or more computer processors to process the one or more measured MRI parameters with one or more simulated MRI parameters for the voxel, the one or more simulated MRI parameters being generated from one or more microstructural models at the voxel; (ii) for the voxel of the plurality of voxels, select a diagnostic model from the one or more microstructural models, the diagnostic model meeting a threshold congruence between the one or more measured MRI parameters and the one or more simulated MRI parameters associated with the diagnostic model; and (iii) for the voxel of the plurality of voxels, use the diagnostic model to determine the disorder state of the brain tissue associated with the voxel.

Each voxel may comprise a plurality of measured MRI parameters. The one or more measured MRI parameters may be a plurality of measured MRI parameters. The one or more simulated MRI parameter may be a plurality of simulated MRI parameters.

The one or more computer processors may be further individually or collectively programmed to repeat (i)-(iii) one or more times for additional voxels of the plurality of voxels. The one or more computer processors may be further individually or collectively programmed to repeat (i)-(iii) for all other voxels of the plurality of voxels. The one or more computer processors may be further individually or collectively programmed to repeat (i)-(iii) for all voxels associated with a specified region of the brain. The one or more computer processors may be further individually or collectively programmed to repeat (i)-(iii) for all voxels associated with an entirety of the brain. The one or more computer processors may be further individually or collectively programmed to repeat (i)-(iii) for a plurality of MRI images, each MRI image of the plurality of MRI images associated with a brain selected from a plurality of brains, each brain of the plurality of brains associated with a subject selected from a plurality of subjects.

The MRI image may be selected from the group consisting of: a longitudinal relaxation time (T1)-weighted MRI image, a transverse relaxation time (T2)-weighted MRI image, and a diffusion-weighted MRI image. The measured MRI parameter may be selected from the group consisting of: a longitudinal relaxation time (T1), a transverse relaxation time (T2), and a diffusion coefficient. The simulated MRI parameter may be selected from the group consisting of: a longitudinal relaxation time (T1), a transverse relaxation time (T2), and a diffusion coefficient.

The one or more microstructural models may comprise information regarding a parameter selected from the group consisting of: intracellular content, extracellular content, distribution of extracellular content within interstitial space, distribution of intracellular content within intracellular space, and tissue geometry. The one or more microstructural models may comprise measured or predicted values of a parameter selected from the group consisting of: cell density, cell shape, cell geometry, cell size, cell distribution, intercellular spacing, extracellular matrix homogeneity, interstitial tortuosity, water to protein ratio, water to lipid ratio, water to carbohydrate ratio, protein to lipid ratio, protein to carbohydrate ratio, and lipid to carbohydrate ratio. The one or more microstructural models may be selected from a microstructural model library. The microstructural model library may comprise at least 100 microstructural models.

The microstructural model library may be constructed by: (a) creating a first microstructural model corresponding to a brain state that is not associated with a disorder; and (b) iteratively subjecting the first microstructural model to a perturbation, each iteration producing an additional perturbed microstructural model. (b) may comprise subjecting the first microstructural model to at least 100 iterations to generate at least 100 perturbed microstructural models. The first microstructural model may be selected based on knowledge of the brain region associated with the voxel. The perturbation may comprise an operation selected from the group consisting of: depleting cells, altering cellular morphology or distribution, altering intracellular or interstitial physico-chemical composition or distribution, altering extracellular matrix composition or distribution, and altering intercellular spacing. The perturbation may comprise a stochastic procedure.

The threshold congruence may be determined by computing an objective function between the one or more measured MRI parameters and the one or more simulated MRI parameters. The objective function may comprise an L1 norm or an L2 norm.

Determining the disorder state of the brain tissue associated with the voxel may be achieved at an accuracy of at least 90%. Determining the disorder state across the brain tissue associated with the specified region of the brain may be achieved at an accuracy of at least 90%. Determining the disorder state of the brain tissue associated with the whole brain of the subject may be achieved at an accuracy of at least 90%. Determining the disorder state of the brain tissue associated the plurality of subjects may be achieved at an accuracy of at least 90%.

The disorder may be a non-neurodegenerative disorder. The disorder may be selected from the group consisting of: a primary neoplasm, a metastatic neoplasm, a seizure disorder, a seizure disorder with focal cortical dysplasia, a demyelinating disorder, a non-neurodegenerative encephalopathy, a cerebrovascular disease, and a psychological disorder. The disorder may be a neurodegenerative disorder. The disorder may be selected from the group consisting of: Alzheimer's disease, a non-Alzheimer's dementia disorder, Parkinson's disease, a Parkinsonism disorder, a motor neuron disease, Huntington's disease, a Huntington's disease-like syndrome, transmissible spongiform encephalopathy, chronic traumatic encephalopathy, and a tauopathy.

The system may enable diagnosis of a neurodegenerative disorder more than 5 years prior to the development of symptoms associated with the neurodegenerative disorder. The system may enable monitoring of the neurodegenerative disorder at a plurality of time points, the plurality of time points separated by a plurality of time intervals.

The one or more computer processors may be further individually or collectively programmed to construct a brain map that, for each voxel of the plurality of voxels, indicates the disorder state of the brain tissue associated with the voxel. The one or more computer processors may be further individually or collectively programmed to display the brain map on a graphical user interface of an electronic device of a user. The brain map may comprise a qualitative abnormality map. The brain map may comprise a binary abnormality map. The brain map may comprise a quantitative abnormality map. The brain map may comprise a percent abnormality map.

In an aspect, a system for determining a disorder state of a tissue in a portion of a body of a subject may comprise: (a) a database comprising magnetic resonance imaging (MRI) data comprising at least one MRI image of the brain, the MRI image comprising a plurality of voxels, a voxel of the plurality of voxels being associated with the brain tissue of the brain of the subject and comprising a measured MRI parameter in the MRI data; and (b) one or more computer processors operatively coupled to the database, wherein the one or more computer processors are individually or collectively programmed to: (i) for the voxel of the plurality of voxels, use one or more computer processors to process the one or more measured MRI parameters with one or more simulated MRI parameters for the voxel, the one or more simulated MRI parameters being generated from one or more microstructural models at the voxel; (ii) for the voxel of the plurality of voxels, select a diagnostic model from the one or more microstructural models, the diagnostic model meeting a threshold congruence between the one or more measured MRI parameters and the one or more simulated MRI parameters associated with the diagnostic model; and (iii) for the voxel of the plurality of voxels, use the diagnostic model to determine the disorder state of the tissue associated with the voxel.

The tissue may be selected from the group consisting of: spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, and non-brain tissue of the head and neck.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
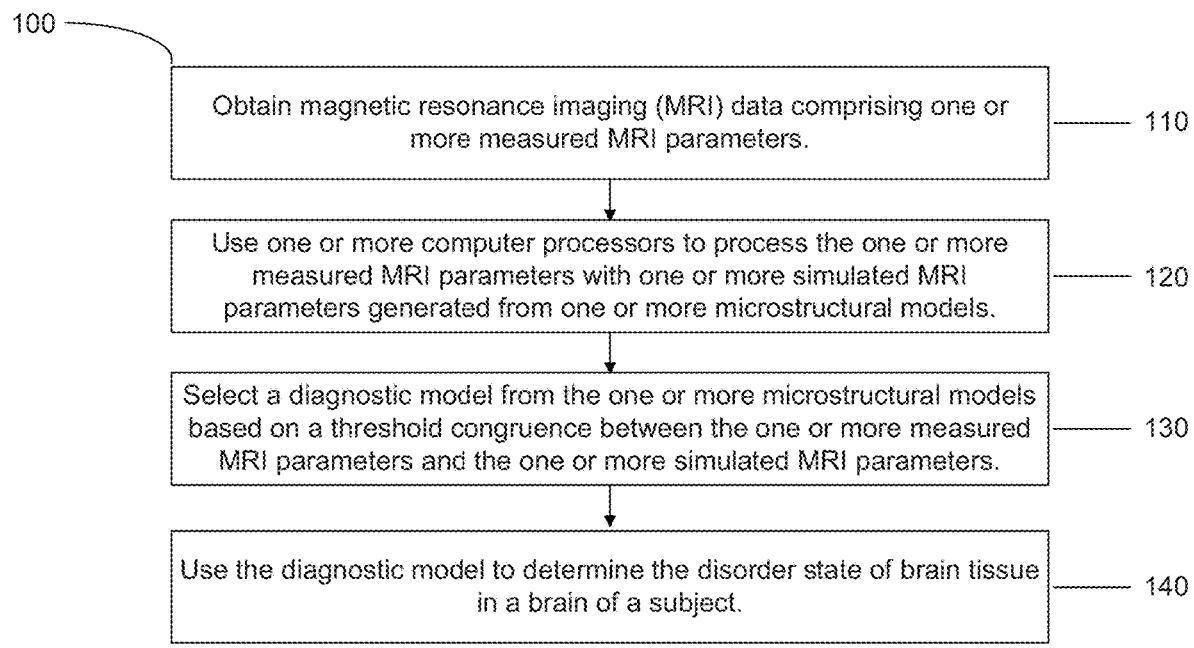
FIG. 1 shows a method for determining a neurological disorder state of brain tissue in a brain of a subject.

While various embodiments of the invention are shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, the term "subject" generally refers to an animal, such as a mammalian species (e.g., human) or avian (e.g., bird) species, or other organism, such as a plant. The subject can be a vertebrate, a mammal, a mouse, a primate, a simian, or a human. Animals may include, but are not limited to, farm animals, sport animals, and pets. A subject can be a healthy or asymptomatic individual, an individual that has or is suspected of having a disease (e.g., a neurological disorder) or a pre-disposition to the disease, or an individual that is in need of therapy or suspected of needing therapy. A subject can be a patient.

As used herein, the term "brain region" (also referred to as "region of a brain" or "region of the brain") generally refers to any sub-structure of a brain. The brain region may be a sub-region or the entirety of a prosencephalon (forebrain), or a sub-region or the entirety of a mesencephalon (midbrain), or a sub-region or the entirety of a rhombencephalon (hindbrain). The brain region may be a medulla oblongata. The brain region may be a medullary pyramid, olivary body, inferior olivary nucleus, rostral ventrolateral medulla, caudal ventrolateral medulla, solitary nucleus, respiratory center, dorsal respiratory group, ventral respiratory group, pre-Botzinger complex, Bötzinger complex, retrotrapezoid nucleus, nucleus retrofacialis, nucleus retroambiguus, nucleus paraambiguus, paramedian reticular nucleus, gigantocellular reticular nucleus, parafacial zone, cuneate nucleus, gracile nucleus, perihypoglossal nucleus, intercalated nucleus, prepositus nucleus, sublingual nucleus, area postrema, medullary cranial nerve nucleus, inferior salivatory nucleus, nucleus ambiguus, dorsal nucleus of the vagus nerve, or hypoglossal nucleus. The brain region may be a pons. The brain region may be a pontine nucleus, pontine cranial nerve nucleus, pontine nucleus of the trigeminal nerve sensory nucleus, motor nucleus for the trigeminal nerve, abducens nucleus, vestibulocochlear nucleus, superior salivatory nucleus, pontine tegmentum, pontine micturition center (Barrington's nucleus), locus coeruleus, pedunculopontine nucleus, laterodorsal tegmental nucleus, tegmental pontine reticular nucleus, parabrachial area, medial parabrachial nucleus, lateral parabrachial nucleus, subparabrachial nucleus (Kölliker-Fuse nucleus), pontine respiratory group, superior olivary complex, paramedian pontine reticular formation, parvocellular reticular nucleus, caudal pontine reticular nucleus, medial nucleus of the trapezoid body, cerebellar peduncle, superior cerebellar peduncle, middle cerebella peduncle, or inferior cerebellar peduncle. The brain region may be a cerebellum. The brain region may be a cerebellar vermis, cerebellar hemisphere, anterior lobe, posterior lobe, flocculonodular lobe, interposed nucleus, globose nucleus, emboliform nucleus, or dentate nucleus. The brain region may be a midbrain (mesencephalon). The brain region may be a tectum. The brain region may be a corpora quadrigemina, inferior colliculi, or superior colliculi. The brain region may be a pretectum. The brain region may be a tegmentum. The brain region may be a periaqueductal gray, rostral interstitial nucleus of medial longitudinal fasciculus, midbrain reticular formation, dorsal raphe nucleus, red nucleus, ventral tegmental area, parabrachial pigmented nucleus, paranigral nucleus, rostromedial tegmental nucleus, caudal linear nucleus, rostral linear nucleus of the raphe, interfascicular nucleus, substantia nigra, pars compact, pars reticulate, or interpeduncular nucleus. The brain region may be a cerebral peduncle. The brain region may be a crus cerebri. The brain region may be a mesencephalic cranial nerve nucleus. The brain region may be an oculomotor nucleus, Edinger-Westphal nucleus, or trochlear nucleus. The brain region may be a mesenchephalic duct (aqueduct of Sylvius). The brain region may be a forebrain (prosencephalon). The brain region may be a diencephalon. The brain region may be an epithalamus. The brain region may be a pineal body, habenular nucleus, stria medullaris, or taenia thalami. The brain region may be a third ventricle. The brain region may be a fourth ventricle. The brain region may be a lateral ventricle. The brain region may be a subcommissural organ. The brain region may be a thalamus. The brain region may be a anteroventral nucleus, anterodorsal nucleus, anteromedial nucleus, medial nuclear group, medial dorsal nucleus, midline nuclear group, paratenial nucleus, reuniens nucleus, rhomboidal nucleus, intralaminar nuclear group, centromedian nucleus, parafascicular nucleus, paracentral nucleus, central lateral nucleus, central medial nucleus, lateral nuclear group, lateral dorsal nucleus, lateral posterior nucleus, pulvinar, ventral nuclear group, ventral anterior nucleus, ventral lateral nucleus, ventral posterior nucleus, ventral posterior lateral nucleus, ventral posterior medial nucleus, metathalamus, medial geniculate body, lateral geniculate body, or thalamic reticular nucleus. The brain region may be a hypothalamus. The brain region may be an anterior hypothalamus, medial area of the anterior hypothalamus, anterior medial preoptic area, medial preoptic nucleus, suprachiasmatic nucleus, paraventricular nucleus, supraoptic nucleus, anterior hypothalamic nucleus, lateral area of the anterior hypothalamus, anterior lateral preoptic area, anterior part of the lateral nucleus, supraoptic nucleus, median preoptic nucleus, periventricular preoptic nucleus, tuberal hypothalamus, medial area of the tuberal hypothalamus, dorsomedial hypothalamic nucleus, ventromedial nucleus, arcuate nucleus, lateral area of the tuberal hypothalamus, tuberal part of the lateral nucleus, lateral tuberal nucleus, posterior hypothalamus, medial area of the posterior hypothalamus, mammillary nucleus, posterior nucleus, lateral area of the posterior hypothalamus, posterior part of the lateral nucleus, optic chiasm, subfornical organ, periventricular nucleus, pituitary stalk, tuber cinereum, tuberal nucleus, or tuberomammillary nucleus. The brain region may be a subthalamus. The brain region may be a subthalamic nucleus or zona incerta. The brain region may be a pituitary gland. The brain region may be a neurohypophysis, pars intermedia (intermediate lobe), or adenohypophysis. The brain region may be a cerebrum (telencephalon). The brain region may be a white matter, centrum semiovale, corona radiate, internal capsule, external capsule, extreme capsule, subcortical cerebrum, hippocampus (medial temporal lobe), dentate gyrus, cornu ammonis, cornu ammonis area 1, cornu ammonis area 2, cornu ammonis area 3, cornu ammonis area 4, amygdala (limbic lobe), central nucleus of the amygdala, medial nucleus of the amygdala, cortical nucleus of the amygdala, basomedial nucleus of the amygdala, lateral nucleus of the amygdala, basolateral nucleus of the amygdala, stria terminalis, bed nucleus of the stria terminalis, claustrum, basal ganglia, striatum, dorsal striatum (neostriatum), putamen, caudate nucleus, ventral striatum, nucleus accumbens, olfactory tubercle, globus pallidus, subthalamic nucleus, basal forebrain, anterior perforated substance, substantia innominate, nucleus basalis, diagonal band of Broca, septal nucleus, medial septal nucleus, lamina terminalis, or the vascular organ of the lamina terminalis. The brain region may be a rhinencephalon (paleopallium). The brain region may be an olfactory bulb, olfactory tract, anterior olfactory nucleus, piriform cortex, anterior commissure, uncus, or periamygdaloid cortex. The brain region may be a cerebral cortex (neopallium). The brain region may be a frontal lobe, frontal lobe cortex, primary motor cortex (precentral gyrus), supplementary motor cortex, premotor cortex, prefrontal cortex, orbitofrontal cortex, dorsolateral prefrontal cortex, frontal lobe gyrus, superior frontal gyrus, middle frontal gyrus, inferior frontal gyrus, paracentral lobule, Brodmann area 4, Brodmann area 6, Brodmann area 8, Brodmann area 9, Brodmann area 10, Brodmann area 11, Brodmann area 12, Brodmann area 24, Brodmann area 25, Brodmann area 32, Brodmann area 33, Brodmann area 44, Brodmann area 45, Brodmann area 46, Brodmann area 47, parietal lobe, parietal lobe cortex, primary somoatosensory cortex, secondary somatosensory cortex, posterior parietal cortex, parietal lobe gyrus, postcentral gyrus, precuneus, posterior cingulate cortex, Brodmann area 1, Brodmann area 2, Brodmann area 3, Brodmann area 5, Brodmann area 7, Brodmann area 23, Brodmann area 26, Brodmann area 29, Brodmann area 31, Brodmann area 39, Brodmann area 40, occipital lobe, occipital lobe cortex, primary visual cortex, secondary visual cortex, third visual cortex, fourth visual cortex, dorsomedial area, middle temporal visual cortex, occipital lobe gyrus, lateral occipital gyrus, cuneus, Brodmann area 17, Brodmann area 18, Brodmann area 19, temporal lobe, temporal lobe cortex, primary auditory cortex, secondary auditory cortex, inferior temporal cortex, posterior inferior temporal cortex, temporal lobe gyrus, superior temporal gyrus, middle temporal gyrus, inferior temporal gyrus, entorhinal cortex, perirhinal cortex, parahippocampal gyrus, fusiform gyrus, Brodmann area 20, Brodmann area 21, Brodmann area 22, Brodmann area 27, Brodmann area 34, Brodmann area 35, Brodmann area 36, Brodmann area 37, Brodmann area 38, Brodmann area 41, Brodmann area 42, medial superior temporal area, insular cortex, cingulate cortex, anterior cingulate cortex, retrosplenial cortex, indusium griseum, Brodmann area 23, Brodmann area 24, Brodmann area 26, Brodmann area 29, Brodmann area 30, Brodmann area 31, or Brodmann area 32. The brain region may be a neural pathway. The brain region may be a superior longitudinal fasciculus, arcuate fasciculus, perforant pathway, thalamocortical radiation, corpus callosum, anterior commissure, interthalamic adhesion, posterior commissure, habenular commissure, fornix, mammillotegmental fasciculus, cerebral peduncle, medial forebrain bundle, medial longitudinal fasciculus, myoclonic triangle, major dopaminergic pathway, mesocortical pathway, mesolimbic pathway, nigrostriatal pathway, tuberorinfundibular pathway, serotonin pathway, raphe nucleus, norepinephrine pathway, locus coeruleus, epinephrine pathway, glutamate pathway, or acetylcholine pathway. The brain region may be a descending fiber. The brain region may be an extrapyramidal system, pyramidal tract, corticospinal tract, lateral corticospinal tract, anterior corticospinal tract, corticopontine fiber, frontopontine fiber, temporopontine fiber, corticobulbar tract, corticomesencephalic tract, tectospinal tract, interstitiospinal tract, rubrospinal tract, rubroolivary tract, olivocerebellar tract, olivospinal tract, vestibulospinal tract, lateral vestibulospinal tract, medial vestibulospinal tract, reticulospinal tract, lateral raphespinal tract, alpha system, or gamma system. The brain region may be a somatosensory system. The brain region may be a posterior column, medial lemniscus pathway, gracile fasciculus, cuneate fasciculus, medial lemniscus, spinothalamic tract, lateral spinothalamic tract, anterior spinothalamic tract, spinomesencephalic tract, spinocerebellar tract, spinoolivary tract, or spinoreticular tract. The brain region may be a visual system. The brain region may be an optic tract or optic radiation. The brain region may be an auditory system. The brain region may be a trapezoid body. The brain region may be a lateral lemniscus. The brain region may be a brain stem. The brain region may be a cranial nerve, terminal nerve, olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, or hypoglossal nerve. The brain region may be a neurovascular system. The brain region may be a middle cerebral artery, posterior cerebral artery, anterior cerebral artery-vertebral artery, basilar artery, circle of Willis, glymphatic system, venous system, or circumventricular organ. The brain region may be a meningeal covering, dura mater, arachnoid mater, pia mater, epidural space, subdural space, subarachnoid space, arachnoid septum, superior cistern, cistern of lamina terminalis, chiasmatic cistern, interpeduncular cistern, pontine cistern, cisterna magna, or spinal subarachnoid space. The brain region may comprise any 1, 2, 3, 4, 5, 6, 7, 8, 9, 10, 20, 30, 40, 50, 60, 70, 80, 90, 100, 200, 300, 400, 500, 600, 700, 800, 900, 1,000, or more than 1,000 brain regions described herein. The brain region may comprise a number of brain regions that is within a range defined by any two of the preceding values.

As used herein, the term "tissue" generally refers to biological tissue. The biological tissue may be from a subject.

As used herein, the term "voxel" generally refers to a unit volume in three-dimensional space. The voxel may correspond to a given three-dimensional volume, such as a volume of biological tissue. In the context of biological tissue, a voxel may represent a unit volume of the tissue or a portion of the tissue. For example, in the brain a voxel may represent a unit volume of the brain. Such unit volume may be generated by a user; for instance, a user may generate the unit volume by selecting one or more parameters in a MRI pulse sequence. In some cases, such unit volume may relate to a biological unit of the tissue. For example, a voxel in the context of the brain may correspond to a neuron, a grouping of neurons, one or more brain regions, or one or more portions of one or more brain regions. A voxel may take a rectilinear form, such as that a cube or rectangular prism. A voxel may be defined by any combination of a first linear dimension, a second linear dimension, and a third linear dimension. The first linear dimension may be at most 10 μm, at most 20 μm, at most 50 μm, at most 100 μm, at most 200 μm, at most 500 μm, at most 1 mm, at most 2 mm, at most 5 mm, or at most 10 mm. The first linear dimension may have a value that is within a range defined by any two of the preceding values. The second linear dimension may be at most 10 μm, at most 20 μm, at most 50 μm, at most 100 μm, at most 200 μm, at most 500 μm, at most 1 mm, at most 2 mm, at most 5 mm, or at most 10 mm. The second linear dimension may have a value that is within a range defined by any two of the preceding values. The third linear dimension may be at most 10 μm, at most 20 μm, at most 50 μm, at most 100 μm, at most 200 μm, at most 500 μm, at most 1 mm, at most 2 mm, at most 5 mm, or at most 10 mm. The third linear dimension may have a value that is within a range defined by any two of the preceding values.

Methods for Determining a State of Tissue

In an aspect, the present disclosure provides methods for determining a state of tissue, such as a disorder state of brain tissue. A method for determining a disorder state of a tissue in a portion of a body of a subject may comprise obtaining magnetic resonance imaging (MRI) data comprising at least one MRI image of the tissue. The MRI image may comprise a plurality of voxels. A voxel of the plurality of voxels may be associated with the tissue of the subject and comprise one or more measured MRI parameters in the MRI data.

Next, for the voxel of the plurality of voxels, one or more computer processors may be used to process the one or more measured MRI parameters with one or more simulated MRI parameters for the voxel. The one or more simulated MRI parameters may be generated from one or more microstructural models at the voxel.

Next, for the voxel of the plurality of voxels, a diagnostic model may be selected from the one or more microstructural models. The diagnostic model may be selected using a threshold congruence between the one or more measured MRI parameters and the one or more simulated MRI parameters associated with the diagnostic model. For the voxel of the plurality of voxels, the diagnostic model may be used to determine the disorder state of the tissue associated with the voxel.

Methods of the present disclosure may be used to determine a disorder state of brain tissue of a subject. A method for determining a disorder state of brain tissue of a subject may comprise obtaining MRI data comprising at least one MRI image of the brain, the MRI image comprising a plurality of voxels, a voxel of the plurality of voxels being associated with the brain tissue of the brain of the subject and comprising one or more measured MRI parameters in the MRI data. Next, for the voxel of the plurality of voxels, one or more computer processors may be used to process the one or more measured MRI parameters with one or more simulated MRI parameters for the voxel. The one or more simulated MRI parameters may be generated from one or more microstructural models at the voxel. For the voxel of the plurality of voxels, a diagnostic model may be selected from the one or more microstructural models. The diagnostic model may meet a threshold congruence between the one or more measured MRI parameters and the one or more simulated MRI parameters associated with the diagnostic model. Next, for the voxel of the plurality of voxels, the diagnostic model may be used to determine the disorder state of the brain tissue associated with the voxel.

Reference will now be made to the figures, wherein like numerals refer to like parts throughout. It will be appreciated that the figures and elements therein are not necessarily drawn to scale.

FIG. 1 shows a method 100 for determining a disorder state of brain tissue in a brain of a subject.

In a first operation 110, the method may comprise obtaining magnetic resonance imaging (MRI) data. The MRI data may comprise MRI data obtained from at least one subject. The MRI data may comprise MRI data obtained from at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, or at least 1,000,000 subjects. The MRI data may comprise MRI data obtained from a number of subjects that is within a range defined by any two of the preceding values. The MRI data may comprise at least one MRI image. The MRI data may comprise at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, or at least 1,000,000 MRI images.

The MRI data may comprise a number of MRI images that is within a range defined by any two of the preceding values. The MRI data may comprise a single MRI image of each brain of each subject of the plurality of subjects. Alternatively, the MRI data may comprise a plurality of MRI images of each brain of each subject, such as at least 2, at least 3, at least 4, at least 5, at least 10, at least 20, at least 50, at least 100, at least 200, at least 500, or at least 1,000 images of each brain of each subject. The number of images for each subject of the plurality of subjects may be the same across all subjects. Alternatively, the number of images for each subject may differ across the subjects.

One or more of the MRI images may comprise a weighted MRI image. One or more MRI images may comprise a longitudinal relaxation time (T1)-weighted MRI image. The one or more T1-weighted MRI images may be obtained by a T1-weighted MRI pulse sequence, such as a T1-weighted spin echo pulse sequence, a T1-weighted gradient echo pulse sequence, a paramagnetic contrast agent (such as gadolinium) enhanced T1-weighted pulse sequence, a T1-weighted Fluid-Attenuated Inversion Recovery (T1-FLAIR) pulse sequence, a fat-suppressed T1-weighted pulse sequence, or any other T1-weighted MRI pulse sequence. One or more MRI images may comprise a transverse relaxation time (T2)-weighted MRI image. The one or more T2-weighted MRI images may be obtained by a T2-weighted MRI pulse sequence, such as a T2-weighted spin echo pulse sequence, a T2-weighted gradient echo pulse sequence, a T2-weighted Fluid-Attenuated Inversion Recovery (T2-FLAIR) pulse sequence, a fat-suppressed T2-weighted pulse sequence, a T2-star pulse sequence, or any other T2-weighted MRI pulse sequence. One or more MRI images may comprise a diffusion-weighted MRI image. The one or more diffusion-weighted MRI images may be obtained by any diffusion-weighted MRI pulse sequence, such as a diffusion-weighted imaging (DWI) pulse sequence, a diffusion tensor imaging (DTI) pulse sequence, or a diffusion kurtosis imaging (DKI) pulse sequence. One or more MRI images may comprise a proton density (PD)-weighted MRI image. The one or more proton density-weighted MRI images may be obtained by any proton density-weighted MRI pulse sequence, such as to a fat-suppressed proton density-weighted pulse sequence. One or more MRI images may comprise a post-processed diffusion-weighted image such as an apparent diffusion coefficient (ADC) image, a mean diffusivity (MD) image, an axial diffusivity (AxD) image, a radial diffusivity (RD) image, or a fractional anisotropy (FA) image. The one or more post-processed diffusion-weighted MRI images may be obtained by post-processing of any diffusion-weighted MRI pulse sequence, such as a diffusion-weighted imaging (DWI) pulse sequence, a diffusion tensor imaging (DTI) pulse sequence, or a diffusion kurtosis imaging (DKI) pulse sequence. One or more MRI images may comprise a susceptibility-weight image, a spoiled gradient echo (SPGR) image, a fast spoiled gradient echo (FSPGR) image, an inversion recovery spoiled gradient echo (IR_SPGR) image, a magnetization prepared rapid gradient echo (MP RAGE) image, or a fluid-attenuated inversion recovery (FLAIR) image. One or more MRI images may comprise a sodium magnetic resonance (sodium MRI) image, a susceptibility-weighted image (SWI), a magnetic resonance spectroscopy (MRS) image, a magnetic resonance fingerprinting (MRF) image, a functional magnetic resonance (fMRI) image, such as a blood-oxygen-level-dependent (BOLD) image, or an arterial spin labeling (ASL) image.

Each MRI image may comprise a plurality of voxels. Each voxel may be associated with brain tissue of the one or more brains of the one or more subjects. Each voxel may comprise one or more measured MRI parameters. The measured MRI parameters may comprise a measured T1 time, a measured T2 time, a measured proton density, a measured diffusion coefficient, a measured diffusivity, a measured fractional anisotropy of diffusion, or a measured diffusion kurtosis. The measured MRI parameters may comprise a plurality of measured MRI parameters. For instance, the measured MRI parameters may comprise a measured T1 time and a measured T2 time, a measured T1 time and a measured diffusion coefficient, a measured T2 time and a measured diffusion coefficient, or a measured T1 time, a measured T2 time, and a measured diffusion coefficient. The number of measured MRI parameters for each voxel may be the same across all voxels, all images, or all subjects. Alternatively, the number of measured MRI parameters for each voxel may differ across the voxels, images, or subjects.

In a second operation 120, the method may comprise using one or more computer processors to process the one or more measured MRI parameters for a voxel of the plurality of voxels. The one or more measured MRI parameters may be processed with one or more simulated MRI parameters.

The simulated MRI parameters may comprise a simulated T1 time, a simulated T2 time, a simulated proton density, a simulated diffusion coefficient, a simulated diffusivity, a simulated fractional anisotropy of diffusion, or a simulated diffusion kurtosis. The simulated MRI parameters may comprise a plurality of simulated MRI parameters. For instance, the simulated MRI parameters may comprise a simulated T1 time and a simulated T2 time, a simulated T1 time and a simulated diffusion coefficient, a simulated T2 time and a simulated diffusion coefficient, or a simulated T1 time, a simulated T2 time, and a simulated diffusion coefficient. The number of simulated MRI parameters for each voxel may be the same across all voxels, all images, or all subjects. Alternatively, the number of simulated MRI parameters for each voxel may differ across the voxels, images, or subjects. The number of simulated MRI parameters for each voxel may be chosen to equal the number of measured MRI parameters for each voxel.

The one or more simulated MRI parameters may be generated from one or more microstructural models at the voxel. The microstructural models may comprise information regarding one or more parameters that may allow computation of one or more of the predicted MRI parameters of a voxel described herein. The microstructural models may comprise information regarding intracellular content of cells that compose brain tissue within a voxel, extracellular content of brain tissue within a voxel, a distribution of extracellular content within interstitial space of the brain tissue within a voxel, a distribution of intracellular content within intracellular space of cells that compose brain tissue within a voxel, or brain tissue geometry.

The microstructural models may comprise measured or predicted values of one or more microstructural model parameters such as cell density within a voxel, cell shape within a voxel, cell geometry within a voxel, cell size within a voxel, cell distribution within a voxel, intercellular spacing within a voxel, extracellular matrix homogeneity within a voxel, interstitial tortuosity within a voxel, water to protein ratio within a voxel, water to lipid ratio within a voxel, water to carbohydrate ratio within a voxel, protein to lipid ratio within a voxel, protein to carbohydrate ratio within a voxel, or lipid to carbohydrate ratio within a voxel.

The one or more microstructural models may be informed by knowledge of a region of the brain in which a given voxel is located. For instance, values of the microstructural model parameters for a voxel associated with a particular region of the brain may be assigned based on experimentally-determined values of the parameters within the given region. Alternatively or in combination, values of the microstructural model parameters for a voxel associated with a particular region of the brain may be assigned based on theoretical predictions of the values of the parameters within the given region. In this manner, the one or more microstructural model parameters may be dependent on the region of the brain with which a voxel is associated, and the microstructural model parameters may be different for other voxels associated with different regions of the brain.

The one or more microstructural models may be selected from one or more microstructural model libraries. Each of the one or more microstructural model libraries may comprise at least 100, at least 200, at least 500, at least 1,000, at least 2,000, at least 5,000, at least 10,000, at least 20,000, at least 50,000, at least 100,000, at least 200,000, at least 500,000, or at least 1,000,000 microstructural models. Each of the one or more microstructural model libraries may comprise a number of microstructural models that is within a range defined by any two of the preceding values. Different microstructural model libraries may be used to select the one or more microstructural models for a given voxel based on the region of the brain with which the voxel is associated. The one or more microstructural model libraries may be constructed using the method 200 described herein.

The operation 120 may comprise using the one or more computer processors to process the one or more measured MRI parameters, or a computed function or transformation of the one or more measured MRI parameters, with the one or more simulated MRI parameters, or a computed function or transformation of the one or more simulated MRI parameters, by computing an objective function between the one or more measured MRI parameters, or a computed function or transformation of the one or more measured MRI parameters, and the one or more simulated MRI parameters, or a computed function or transformation of the one or more measured MRI parameters, generated from the one or more microstructural models. The objective function may comprise an L1 norm, an L2 norm, or any other objective function.

The objective function may comprise an L1 norm computed between a measured MRI parameter and a simulated MRI parameter, or an L1 norm computed between any 2, 3, 4, 5, 6, 7, 8, 9, 10, or more than 10 measured MRI parameters and any 2, 3, 4, 5, 6, 7, 8, 9, 10, or more than 10 simulated parameters, respectively. For instance, the objective function may comprise an L1 norm computed between a measured T1 time and a simulated T1 time, an L1 norm computed between a measured T2 time and a simulated T2 time, an L1 norm computed between a measured diffusion coefficient and a simulated diffusion coefficient, an L1 norm computed between a measured T1 time and a simulated T1 time, and a measured T2 time and a simulated T2 time, an L1 norm computed between a measured T1 time and a simulated T1 time, and a measured diffusion coefficient and a simulated diffusion coefficient, an L1 norm computed between a measured T2 time and a simulated T2 time, and a measured diffusion coefficient and a simulated diffusion coefficient, or an L1 norm computed between a measured T1 time and a simulated T1 time, a measured T2 time and a simulated T2 time, and a measured diffusion coefficient and a simulated diffusion coefficient.

The objective function may comprise an L2 norm computed between a measured MRI parameter and a simulated MRI parameter, or an L2 norm computed between any 2, 3, 4, 5, 6, 7, 8, 9, 10, or more than 10 measured MRI parameters and any 2, 3, 4, 5, 6, 7, 8, 9, 10, or more than 10 simulated MRI parameters, respectively. For instance, the objective function may comprise an L2 norm computed between a measured T1 time and a simulated T1 time, an L2 norm computed between a measured T2 time and a simulated T2 time, an L2 norm computed between a measured diffusion coefficient and a simulated diffusion coefficient, an L2 norm computed between a measured T1 time and a simulated T1 time, and a measured T2 time and a simulated T2 time, an L2 norm computed between a measured T1 time and a simulated T1 time, and a measured diffusion coefficient and a simulated diffusion coefficient, an L2 norm computed between a measured T2 time and a simulated T2 time, and a measured diffusion coefficient and a simulated diffusion coefficient, or an L2 norm computed between a measured T1 time and a simulated T1 time, a measured T2 time and a simulated T2 time, and a measured diffusion coefficient and a simulated diffusion coefficient.

The objective function may comprise a weighted L1 norm or a weighted L2 norm. The objective function may comprise a Mahalanobis distance. The objective function may comprise an explicit formula derived from a single simulated microstructural model or combinations of simulated microstructural models.

In an operation 130, the method may comprise selecting one or more diagnostic models from the one or more microstructural models for a voxel of the plurality of voxels. The one or more diagnostic models may be selected by computing an objective function for each of the one or more microstructural models; the objective function may be any objective function described herein. The objective function for each microstructural model may be tested against a threshold and one or more microstructural models may be selected as a diagnostic model if the objective function for the given microstructural model meets a threshold congruence. In some cases, one diagnostic model may be chosen (such as the diagnostic model which minimizes the objective function). In other cases, a plurality of diagnostic models, such as at least 2, at least 3, at least 4, at least 5, at least 6, at least 7, at least 8, at least 9, at least 10, or at least 10 diagnostic models may be chosen (for instance, when a plurality of microstructural models meets the threshold congruence).

In an operation 140, the method may comprise using the one or more diagnostic models to determine the disorder state of the brain tissue associated with a voxel of the plurality of voxels. The one or more diagnostic models may indicate a healthy brain tissue state, based on knowledge of the microstructure associated with the diagnostic models. For instance, diagnostic models that are similar in microstructure to a known healthy microstructure may be indicative of a healthy brain tissue state; alternatively or in combination, diagnostic models that are dissimilar in microstructure to a known diseased microstructure may be indicative of a healthy brain tissue state. The one or more diagnostic models may indicate a diseased brain tissue state, again based on knowledge of the microstructure associated with the diagnostic models. For instance, diagnostic models that are dissimilar in microstructure to a known healthy microstructure may be indicative of a diseased brain tissue state; alternatively or in combination, diagnostic models that are similar in microstructure to a known diseased microstructure may be indicative of a diseased brain tissue state.

The one or more diagnostic models may comprise qualitative or quantitative information related to an extent to which brain tissue associated with a given voxel has progressed from a healthy state to a diseased state.

The selection of a plurality of diagnostic models may serve as a check as to whether the method has accurately determined the disorder state of the brain tissue associated with the voxel. For instance, the plurality of diagnostic models may be compared to one another. If most or all of the plurality of diagnostic models are associated with a healthy brain state for a given voxel, this may instill greater confidence that the method has accurately determined that brain tissue associated with the voxel is healthy. If most or all of the plurality of diagnostic models are associated with a diseased brain state for a given voxel, this may instill greater confidence that the method has accurately determined that brain tissue associated with the voxel is diseased. If the plurality of diagnostic models are not in agreement as to whether the brain tissue is associated with a healthy or a diseased state, this may instill poor confidence that the method has accurately determined the disorder state of brain tissue associated with the voxel.

The method 100 may be applied to a single voxel of the plurality of voxels. The method may be applied to additional voxels of the plurality of voxels. For instance, operations 120, 130, and 140 may be repeated one or more times for additional voxels of the plurality of voxels. The method may be applied to all other voxels of the plurality of voxels. For instance, operations 120, 130, and 140 may be repeated for all other voxels of the plurality of voxels. The method may be applied to all voxels associated with a specified region of the brain. For instance, operations 120, 130, and 140 may be repeated one or more times for all voxels associated with a specified region of the brain. The method may be applied to all voxels associated with an entirety of the brain. For instance, operations 120, 130, and 140 may be repeated one or more times for all voxels associated with an entirety of the brain. The method may be applied to a plurality of MRI images. For instance, operations 110, 120, 130, and 140 may be repeated one or more times for a plurality of MRI images. Each MRI image of the plurality of images may be associated with a brain selected from a plurality of brains. Each brain of the plurality of brains may be associated with a subject selected from a plurality of subjects.

Figure 2:
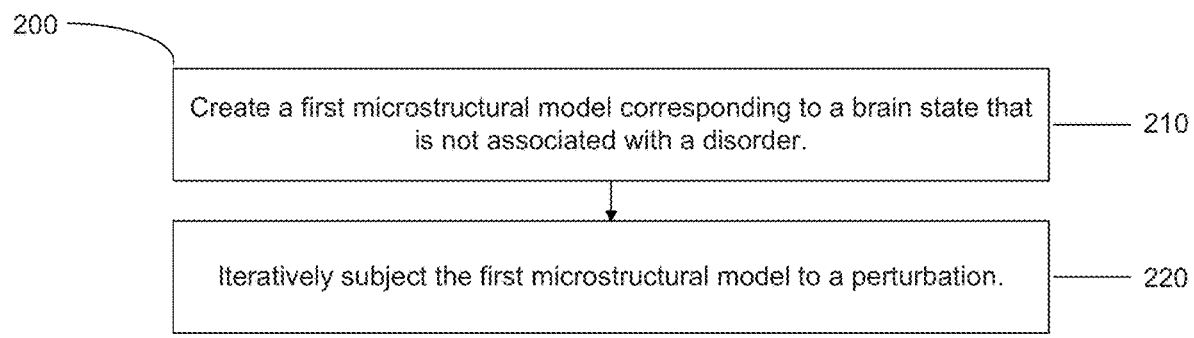
FIG. 2 shows a method for constructing a microstructural model library.

FIG. 2 shows a method 200 for constructing a microstructural model library.

In a first operation 210, the method may comprise creating a first microstructural model corresponding to a brain state that is not associated with a disorder.

In a second operation 220, the method may comprise iteratively subjecting the first microstructural model to a perturbation. Each iteration may produce an additional perturbed microstructural model. The first microstructural model may be selected based on knowledge of the brain region associated with the voxel. For instance, the first microstructural model may be informed by knowledge of a region of the brain in which a given voxel is located, as described herein.

The first microstructural model may be subjected to at least 100 iterations, at least 200 iterations, at least 500 iterations, at least 1,000 iterations, at least 2,000 iterations, at least 5,000 iterations, at least 10,000 iterations, at least 20,000 iterations, at least 50,000 iterations, at least 100,000 iterations, at least 200,000 iterations, at least 500,000 iterations, or at least 1,000,000 iterations to generate at least 100 perturbed microstructural models, at least 200 perturbed microstructural models, at least 500 perturbed microstructural models, at least 1,000 perturbed microstructural models, at least 2,000 perturbed microstructural models, at least 5,000 perturbed microstructural models, at least 10,000 perturbed microstructural models, at least 20,000 perturbed microstructural models, at least 50,000 perturbed microstructural models, at least 100,000 perturbed microstructural models, at least 200,000 perturbed microstructural models, at least 500,000 perturbed microstructural models, or at least 1,000,000 perturbed microstructural models, respectively. The first microstructural model may be subjected to a number of iterations that is within a range defined by any two of the preceding values to generate a number of perturbed microstructural models that is within a range defined by any two of the preceding values.

Each iteration may comprise one or more operations that alter one or more parameters of the first microstructural model or subsequent altered iterations of the first microstructural model. The one or more operations may comprise depleting cells, altering cellular morphology or distribution, altering intracellular or interstitial physico-chemical composition or distribution, altering extracellular matrix composition or distribution, or altering intercellular spacing. Each iteration may comprise a stochastic procedure, such as a Monte Carlo procedure.

Many variations, alterations, and adaptations based on the methods 100 or 200 provided herein are possible. For example, the order of the operations of the methods 100 or 200 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

The methods 100 or 200 described herein may be used to determine the disorder state of the brain tissue associated with a voxel at any accuracy greater than or equal to 60%, 65%, 70%, 75%, 80%, 85%, 90%, 95%, 99%, or greater. The methods may be used to determine the disorder state of the brain tissue associated with a voxel at an accuracy that is within a range defined by any two of the preceding values.

Methods of the present disclosure may be used to determine the disorder state across the brain tissue associated with a specified region of the brain at an accuracy greater than or equal to about 60%, 65%, 70%, 75%, 80%, 85%, 90%, 95%, 99%, or greater. The methods may be used to determine the disorder state across the brain tissue associated with a specified region of the brain at an accuracy that is within a range defined by any two of the preceding values.

Methods of the present disclosure may be used to determine the disorder state across the brain tissue associated with the whole brain of a subject at an accuracy greater than or equal to about 60%, 65%, 70%, 75%, 80%, 85%, 90%, 95%, 99%, or greater. The methods may be used to determine the disorder state across the brain tissue associated with the whole brain of a subject at an accuracy that is within a range defined by any two of the preceding values.

Methods of the present disclosure may be used to determine the disorder state across the brain tissue associated with a plurality of subjects at an accuracy greater than or equal to about 60%, 65%, 70%, 75%, 80%, 85%, 90%, 95%, 99%, or greater. The methods may be used to determine the disorder state across the brain tissue associated with a plurality of subjects at an accuracy that is within a range defined by any two of the preceding values.

Methods of the present disclosure may be used to diagnose a non-neurodegenerative disorder. The non-neurodegenerative disorder may be a primary neoplasm, a metastatic neoplasm, a seizure disorder, a seizure disorder with focal cortical dysplasia, a demyelinating disease (such as multiple sclerosis), a non-neurodegenerative encephalopathy (such as a hypertensive encephalopathy, an ischemic encephalopathy, a metabolic encephalopathy, or an infectious encephalopathy), a cerebrovascular disease (such as stroke or transient ischemic attack), or a psychological disorder (such as schizophrenia, a schizophreniform disorder, autism, an autism spectrum disorder, depression, bipolar disorder, or obsessive compulsive disorder).

Methods of the present disclosure may be used to diagnose a neurodegenerative disorder. In some cases, the methods may be used to diagnose a neurodegenerative disorder at least 5 years, at least 10 years, at least 15 years, or at least 20 years prior to the development of symptoms associated with the neurodegenerative disorder. The methods may be used to diagnose a neurodegenerative disorder in a time period prior to the development of symptoms associated with the neurodegenerative disorder that is within a range defined by any two of the preceding values. The neurodegenerative disorder may be Alzheimer's disease, a non-Alzheimer's dementia disorder, Parkinson's disease, a Parkinsonism disorder, a motor neuron disease (such as amyotrophic lateral sclerosis), Huntington's disease, a Huntington's disease-like syndrome, a transmissible spongiform encephalopathy, chronic traumatic encephalopathy, a tauopathy (such as Pick's disease, corticobasal degeneration, progressive supranuclear palsy, or Nieman-Pick disease), or any other neurodegenerative disorder.

Methods of the present disclosure may further comprise constructing one or more brain maps. The one or more brain maps may indicate the neurodegenerative disorder state of the brain tissue associated with each voxel of a plurality of voxels. The methods may comprise display of the one or more brain maps on a graphical user interface (GUI) of an electronic device of a user.

The one or more brain maps may comprise a qualitative abnormality map (such as a qualitative neurodegeneration map). The qualitative abnormality map may display whether brain tissue associated with a given voxel displays a microstructure consistent with a brain disorder (such as a neurodegenerative disorder), for each voxel of the plurality of voxels. The qualitative abnormality map may be a binary map, with each voxel assigned a microstructure consistent with a brain disorder displayed in the same color (such as gray or red) on the qualitative abnormality map. The determination of whether the given voxel displays a microstructure that is consistent with a brain disorder may be subject to a thresholding procedure. For instance, a qualitative neurodegeneration map may only indicate that a given voxel is indicative of a neurodegenerative disorder if the microstructure associated with the voxel displays some threshold level of neurodegeneration. The thresholding procedure may allow a viewer of the qualitative neurodegeneration map to ignore minimal neurodegeneration and to instead focus their attention on more severely compromised areas of the brain. The qualitative abnormality map may be a percent abnormality map (such as a percent neurodegeneration (PND) map) that indicates a percentage of a subject's brain (or region of a subject's brain) that displays tissue microstructure consistent with a brain disorder (such as a neurodegenerative disorder).

The qualitative abnormality map may indicate whether brain tissue associated with a given brain region displays a microstructure consistent with a brain disorder (such as a neurodegenerative disorder), for each brain region of the plurality of brain regions. The qualitative abnormality map may be a binary map, with each brain region assigned a microstructure consistent with a brain disorder displayed in the same color (such as gray or red) on the qualitative abnormality map. The determination of whether the given brain region displays a microstructure that is consistent with a brain disorder may be subject to a thresholding procedure. For instance, a qualitative neurodegeneration map may only indicate that a given brain region is indicative of a neurodegenerative disorder if the microstructure associated with the brain region displays some threshold level of neurodegeneration. The thresholding procedure may allow a viewer of the qualitative neurodegeneration map to ignore minimal neurodegeneration and to instead focus their attention on more severely compromised areas of the brain.

Alternatively or in combination, the one or more brain maps may comprise a quantitative abnormality map, such as a quantitative neurodegeneration (QND) map.

The QND map may display the extent to which brain tissue associated with a given voxel displays a microstructure consistent with a neurodegenerative disorder, for each voxel of the plurality of voxels. The determination of the extent to which the brain tissue associated the given voxel displays a microstructure that is consistent with a brain disorder may be subject to a thresholding procedure. The QND map may be a continuous map, with each voxel assigned a microstructure consistent with a neurodegenerative disorder displayed in a color representing the extent to which the brain tissue at the given voxel has been damaged by the neurodegenerative disorder on the QND map. For instance, the QND map may display voxels associated with brain tissue that shows little evidence of neurodegeneration displayed in one color (such as blue), voxels associated with brain tissue that shows evidence of extensive neurodegeneration shown in another color (such as red), and voxels associated with brain tissue that shows evidence of intermediate neurodegeneration shown in other colors (such as yellow or orange) based on the extent to which the brain tissue at the given voxel has been damaged by the neurodegenerative disorder. Alternatively, the QND map may use a gradient of a single color to represent the extent to which each voxel has been damaged by the neurodegenerative disorder. The QND map may use a gradient of a single color (such as gray) to represent the extent of normal variation in the voxels that have not been damaged by the neurodegenerative disorder. The QND map may use any color scheme.

The QND map may display the extent to which brain tissue associated with a given brain region displays a microstructure consistent with a neurodegenerative disorder, for each brain region of the plurality of brain regions. The determination of the extent to which the brain tissue associated the given brain region displays a microstructure that is consistent with a brain disorder may be subject to a thresholding procedure. The QND map may be a continuous map, with each brain region assigned a microstructure consistent with a neurodegenerative disorder displayed in a color representing the extent to which the brain tissue at the given brain region has been damaged by the neurodegenerative disorder on the QND map. For instance, the QND map may display brain regions associated with brain tissue that shows no evidence of neurodegeneration displayed in one color (such as blue), brain regions associated with brain tissue that shows evidence of extensive neurodegeneration shown in another color (such as red), and brain regions associated with brain tissue that shows evidence of intermediate neurodegeneration shown in other colors (such as yellow or orange) based on the extent to which the brain tissue at the given brain region has been damaged by the neurodegenerative disorder. Alternatively, the QND map may use a gradient of a single color to represent the extent to which each brain region has been damaged by the neurodegenerative disorder. The QND map may use a gradient of a single color (such as gray) to represent the extent of normal variation in the brain regions that have not been damaged by the neurodegenerative disorder. The QND map may use any color scheme.

Methods of the present disclosure may further comprise constructing one or more data tables. The one or more data tables may indicate the neurodegenerative disorder state of the brain tissue associated with each voxel of a plurality of voxels. The neurodegenerative disorder state of the brain tissue associated with each voxel may be represented by a quantitative neurodegeneration (QND) score. Alternatively or in combination, the one or more data tables may indicate the neurodegenerative disorder state of the brain tissue associated with one or more regions of a brain. The neurodegenerative disorder state of the brain tissue associated with each region may be represented by a percent neurodegeneration (PND) score and/or a quantitative neurodegeneration (QND) score and/or any other representative independent or composite score or scores. The one or more data tables may indicate the neurodegenerative disorder state of the entirety of a brain. The neurodegenerative disorder state of the entirety of a brain may be represented by a percent neurodegeneration (PND) score and/or quantitative neurodegeneration (QND) score and/or any other representative independent or composite score. The PND score may indicate a percentage of a subject's brain (or percentage of a region or regions of a subject's brain) that displays tissue microstructure consistent with a brain disorder (such as a neurodegenerative disorder). The QND score may indicate the extent to which the brain tissue associated with a given voxel, or a given region of a subject's brain, or the entirety of a subject's brain, displays tissue microstructure consistent with a brain disorder (such as a neurodegenerative disorder).

The other representative independent or composite score or scores described herein may comprise a mathematical combination of multiple measures for a given voxel, plurality of voxels, region, plurality of regions, or whole brains. For example, the composite score may be an estimated neurodegeneration score (END score) comprising a mathematical operation of more than one region measure such as the product of PND and QND. The mathematical operation may comprise multiplying PND and QND scores and dividing the result by 100. The other representative independent or composite score or scores may be derived by computing other parameters such as heterogeneity, asymmetry, or clustering of the voxels or brain regions that display a microstructure that is consistent with a brain disorder, within a brain region, a plurality of brain regions, or an entirety of a subject's brain. The determination of whether a given voxel, a plurality of voxels, a region, a plurality of regions of a subject's brain or a plurality of subjects' brains display a microstructure that is consistent with a brain disorder may be subject to a thresholding procedure. The other representative independent or composite score or scores may be derived by computing other parameters such as heterogeneity, asymmetry, or clustering of the voxels or brain regions that display a microstructure that is consistent with a healthy state of brain tissue. The other representative independent or composite score or scores may be a whole brain score (WBS). The WBS may indicate the extent to which the entirety of a subject's brain displays tissue microstructure consistent with a brain disorder (such as a neurodegenerative disorder). The whole brain score may be expressed by a real number. Similarly, the PND score, the QND score, and the other representative independent or composite score or scores may be expressed by a real number.

Data produced by methods of the present disclosure, alone or in combination with the data tables described herein or the brain maps described herein, may be analyzed using machine learning procedures to improve the accuracy of diagnosis of neurodegenerative disorders. The machine learning procedures may comprise various supervised machine learning techniques, various semi-supervised machine learning techniques, and/or various unsupervised machine learning techniques. For instance, the machine learning procedures may utilize autoencoders, stacked autoencoders, neural networks, convolutional neural networks, alternating decision trees (ADTree), Decision Stumps, functional trees (FT), logistic model trees (LMT), logistic regression, Random Forests, linear classifiers, factor analysis, principle component analysis, neighborhood component analysis, sparse filtering, stochastic neighbor embedding, or any other machine learning algorithm or statistical algorithm. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Machine learning analyses may be performed using one or more of various programming languages and platforms, such as R, Weka, Python, and/or Matlab, for example. Machine learning analyses may be performed using a machine learning platform, such as BigML.

Methods of the present disclosure may be used to inform drug development. For instance, the methods may be used to assess the efficacy of pharmaceutical interventions for neurodegenerative disorders. Since the methods may allow diagnosis of a neurodegenerative disorder during the earliest stages of the disorder, the methods may allow pharmaceuticals to be tested on a cohort of subjects at a much earlier stage in the progression of the neurodegenerative disorder, when minimal damage to brain tissue has occurred and pharmaceutical interventions may be more effective. The methods may allow accurate tracking of neurodegeneration following the administration of a pharmaceutical. The methods, alone or in combination with prior methods, may also allow more accurate selection of patients for clinical trials. For instance, the methods may ensure that only those subjects displaying certain levels or patterns of neurodegeneration are included in a given clinical trial.

Methods of the present disclosure may enable monitoring of brain disorders (such as neurodegenerative disorders) at a plurality of time points, such as at least 2, at least 5, at least 10, at least 20, at least 50, at least 100, at least 200, at least 500, or at least 1,000 time points. The methods may enable monitoring of brain disorders for a number of time points that is within a range defined by any two of the preceding values. Each pair of the plurality of time points may be separated by a plurality of time intervals. For instance, each pair of time points may be separated by at least 1 day, at least 2 days, at least 5 days, at least 1 week, at least 2 weeks, at least 1 month, at least 2 months, at least 5 months, at least 10 months, at least 1 year, at least 2 years, at least 5 years, at least 10 years, at least 20 years, at least 50 years, or at least 100 years. Each of the time points may be separated by a period of time that is within a range defined by any two of the preceding values. In this manner, the methods may be used to track the development or progression of a brain disorder over a period of time.

Though described herein with respect to determining a disorder state of brain tissue, the methods and systems of the present disclosure, such as the methods 100 and 200, may be utilized to determine a state (e.g., disorder state) of other tissues. For instance, methods and systems of the present disclosure may be utilized to determine a disorder state of spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, or non-brain tissues of the head and neck (such as soft tissues of the skull base, tissues of facial structures such as the eyes, nose or ears, tissues of the oral cavity such as the tongue, uvula, gingiva, or palatine tonsils, or deep structures of the neck such as the retropharyngeal space, the para-pharyngeal space, epiglottis, larynx, or trachea).

Though described herein with respect to analysis of MRI images, the methods and systems of the present disclosure, such as the methods 100 and 200, may be utilized to analyze images obtained by other medical imaging technologies. For instance, the methods may allow analysis of images obtained through X-ray computed tomography (CT) imaging, single photon emission computed tomography (SPECT) imaging, electron paramagnetic resonance (EPR) imaging, positron emission tomography (PET) imaging, ultrasound imaging, or any combination of such imaging technologies.

Figure 3:
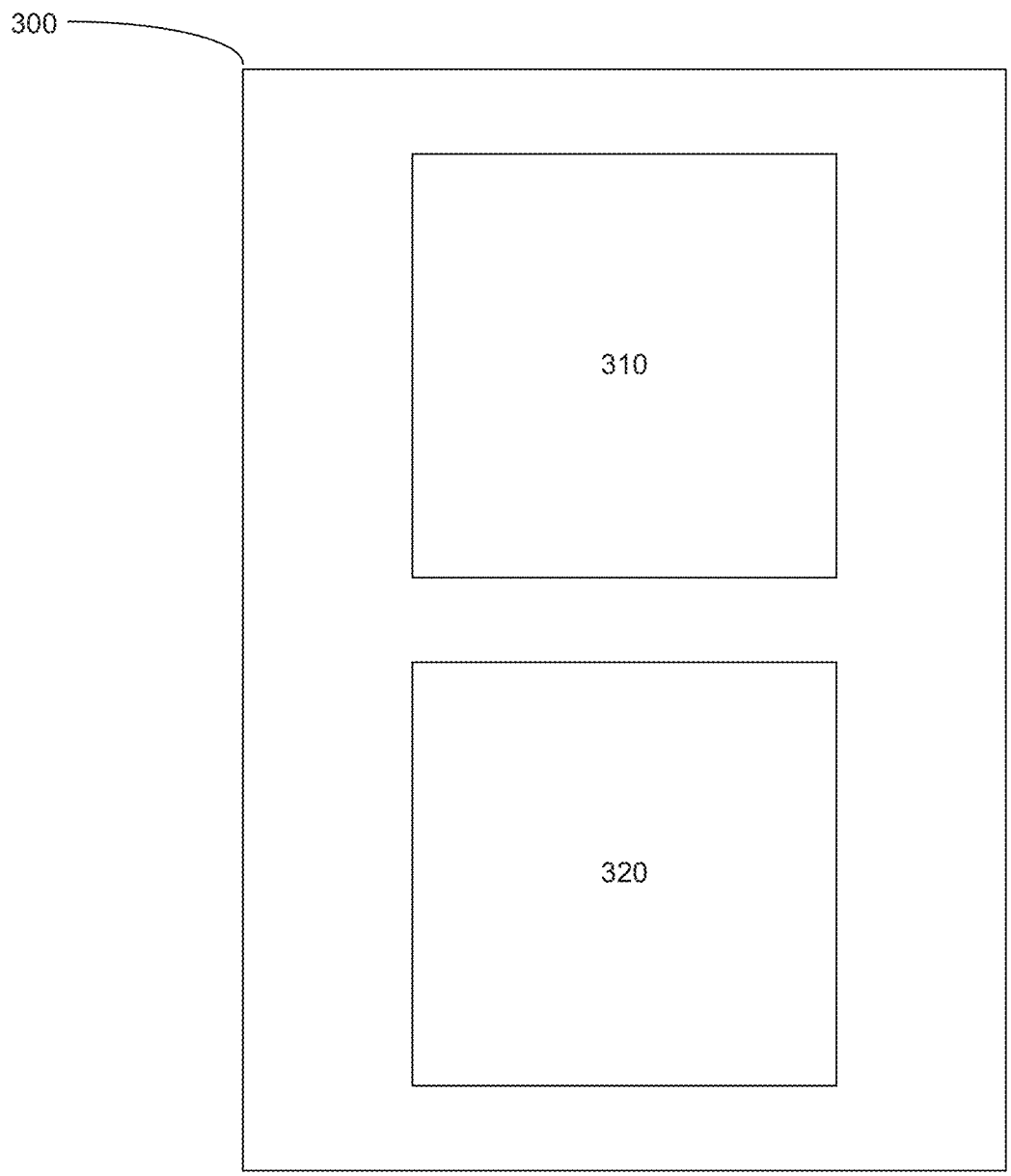
FIG. 3 shows a method for determining a neurological disorder state of brain tissue in a brain of a subject.

FIG. 3 shows a system 300 for determining a disorder state of brain tissue in a brain of a subject. The system may comprise a database 310. The database may comprise any MRI data described herein. For instance, the database may comprise any MRI data described herein with respect to the method 100 or the method 200. The system may further comprise one or more computer processors 320. The one or more processors may be individually or collectively programmed to implement any of the methods described herein. For instance, the one or more processors may be individually or collectively programmed to implement any or all operations of the methods of the present disclosure, such as methods 100 or 200.

Figure 4:
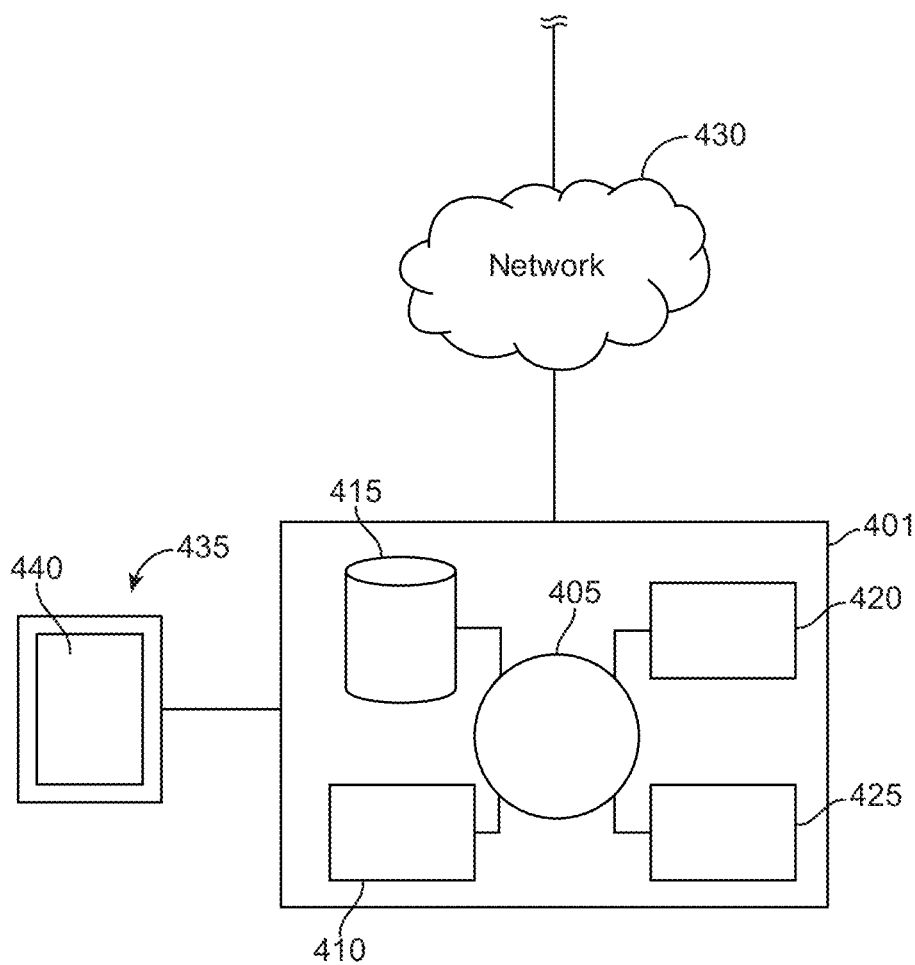
FIG. 4 shows a computer system that is programmed or otherwise configured to operate a system or method for determining a disorder state of brain tissue in a subject.

FIG. 4 shows a computer system 401 that is programmed or otherwise configured to operate a system or method for determining a disorder state of brain tissue in a subject described herein. The computer system 401 can regulate various aspects of the present disclosure. The computer system 401 can be an electronic device of a user or a computer system that is remotely located with respect to the electronic device. The electronic device can be a stationary electronic device such as a desktop computer. The electronic device can be a mobile electronic device.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or "machine readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, determine a disorder state of brain tissue in a subject described herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1: Relation of Microstructure to MRI

FIG. 5 shows the construction of exemplary microstructural models.

Figure 5A:
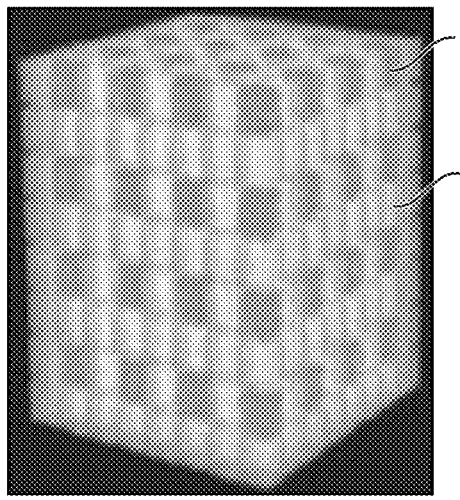
FIG. 5A shows a portion of a cell array for a normal tissue microstructural model.

The first step is construction of a normal tissue microstructural model. The normal tissue microstructural model includes known measured or predicted values of cell density, cell shape, cell geometry, cell size, intercellular spacing, extracellular matrix heterogeneity, interstitial tortuosity, water to lipid ratio, and other tissue parameters that can influence structural and diffusion measurements. Typical ensembles consist of 1024×1024×1024 cell arrays. FIG. 5A shows a portion of a cell array for a normal tissue microstructural model. As shown in FIG. 5A, gray cubes 510 represent brain cells and green spots 520 represent molecular obstacles of the extracellular space.

Figure 5B:
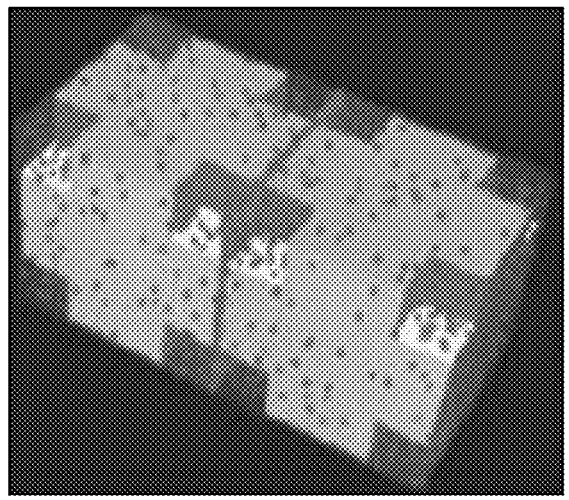
FIG. 5B shows a sample Monte Carlo simulation with delivery of freely moving molecules.

The normal tissue microstructural model is then used for finite-element and Monte Carlo simulations of the tissue chemical composition, tissue micro-lattice topography, and molecular kinetics, which can subsequently be used to generate predicted structural MRI signals (T1-weighted, T2-weighted, and diffusion-weighted MRI signals) and the associated bulk diffusion coefficients. By modifying the range of input parameters in the model, the sensitivity of the output signal values is determined. The reconstructed tissue and calculated values can be directly correlated to MRI values at a single voxel. FIG. 5B shows a sample Monte Carlo simulation with delivery of freely moving molecules. As shown in FIG. 5B, red dots represent areas of abnormal molecular distribution and blue dots represent areas of normal molecular distribution.

Figure 5C:
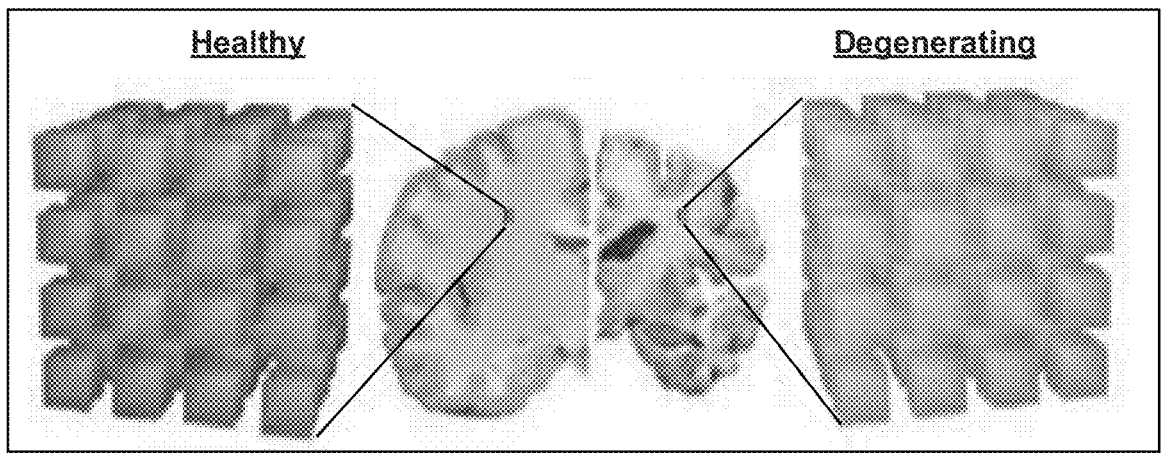
FIG. 5C shows representative models of healthy and degenerating brain tissue.

By manipulating structural components independently and in concert (such as depleting cells, altering morphology, altering interstitial obstructions, etc.) according to reported and predicted variations in brain tissue, the platform may be used to generate a continuous range of tissue transitions from healthy to severe degeneration. FIG. 5C shows representative models of healthy and degenerating brain tissue.

Through in-silico modeling, a database consisting of many possible variations of tissue structure that represent a range of healthy and diseased states that can be directly translated to MRI scan values has been assembled. With this reference set correlating a variation of microstructure composition to MR signals, real human T1-weighted, T2-weighted and diffusion-weighted MRI scans can be applied to predict the most probable tissue microstructure contained in each MRI voxel. The platform may thus be regarded as providing a virtual tissue microscope.

Example 2: Interpretation of Human MRI

Figure 6:
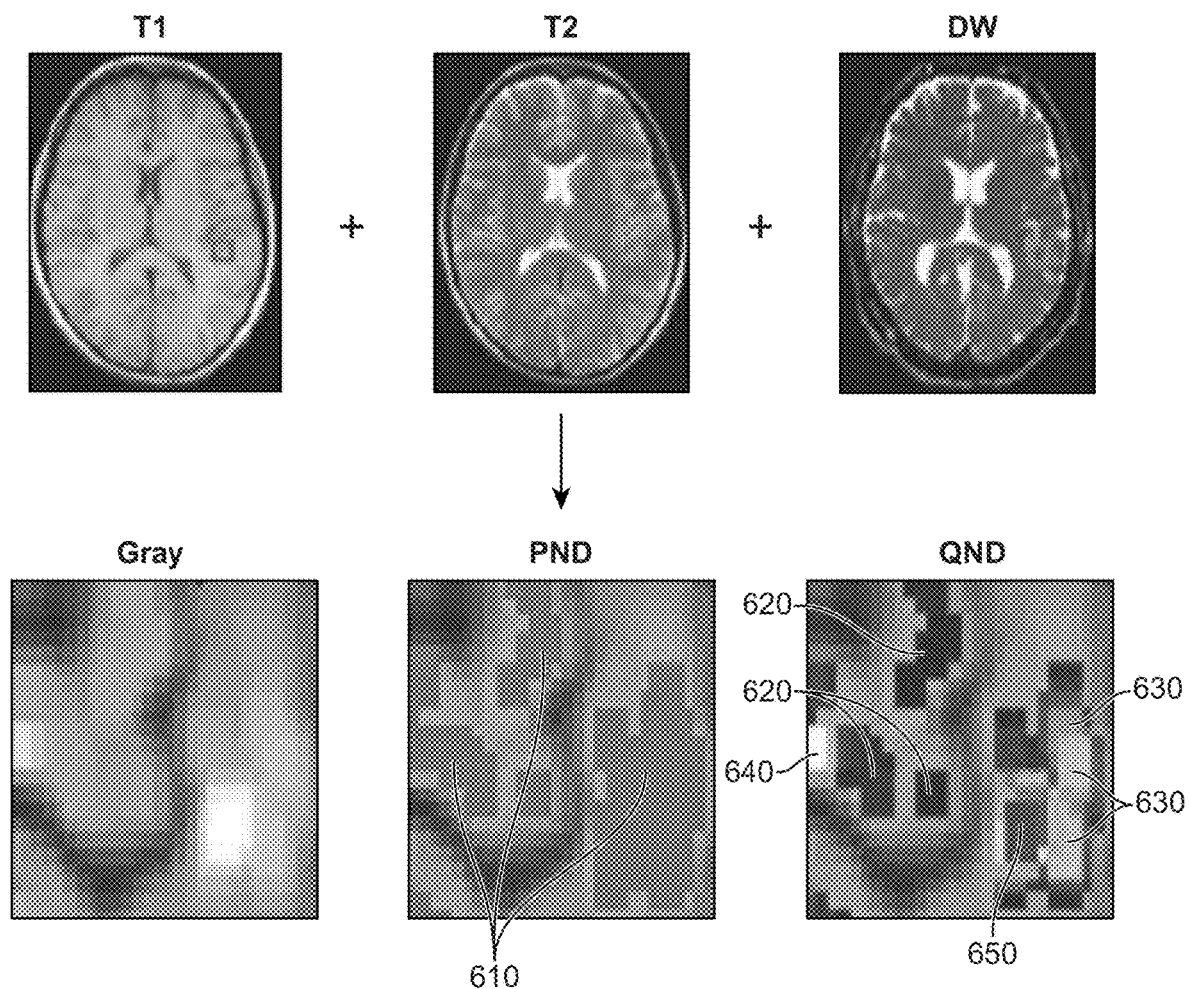
FIG. 6 shows the processing of human magnetic resonance imaging (MRI) images to produce neurodegeneration maps.

FIG. 6 shows the processing of human MRI images to produce neurodegeneration maps.

With a rigorous pipeline for structural prediction of MRI, each voxel of the human brain scan can be comprehensively characterized. The resulting output is a gray map with voxel-wise intensity scaling to represent the predicted deviation from normal.

Based on literature knowledge and initial experimental measurements, it is determined if the calculated tissue structure from a given combination of T1 time, T2 time, and diffusion coefficient values is within tolerance for healthy brain tissue or resides in the spectrum of abnormality. Each voxel 610 determined abnormal is coded red or a variable color, respectively denoting binary (percent neurodegeneration, PND) or quantitative (quantitative neurodegeneration, QND) abnormality in output maps. In effect, PND identifies the abnormal voxels (red) and QND defines how abnormal those voxels are. The range is from dark blue 620 (close to normal) to light blue 630 (slightly abnormal) to yellow 640 (moderately abnormal) to dark red 650 (very abnormal).

Example 3: Generation of PND and QND Brain Maps

Figure 7:
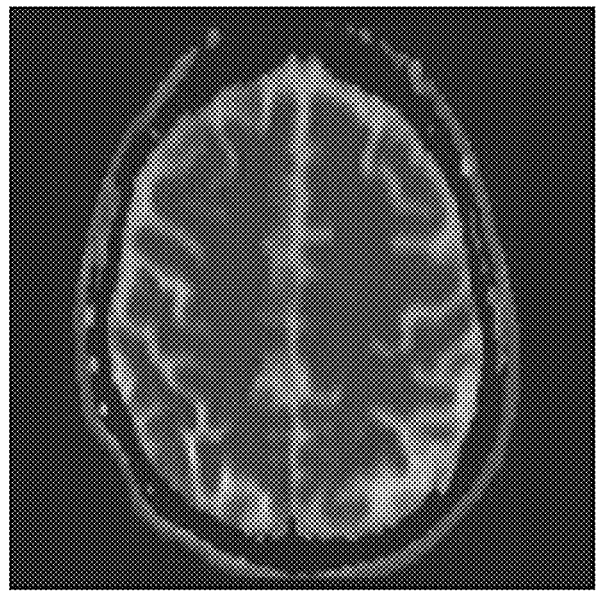
FIG. 7 shows examples of MRI, percent neurodegeneration (PND), and quantitative neurodegeneration (QND) brain maps from a diseased individual.
Figure 7:
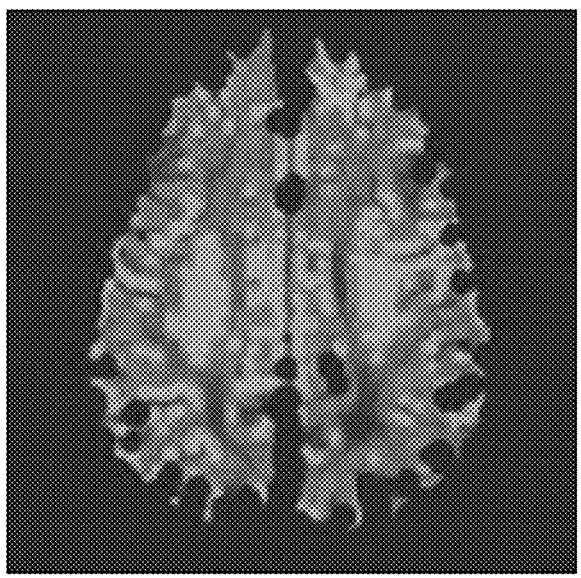
Figure 7:
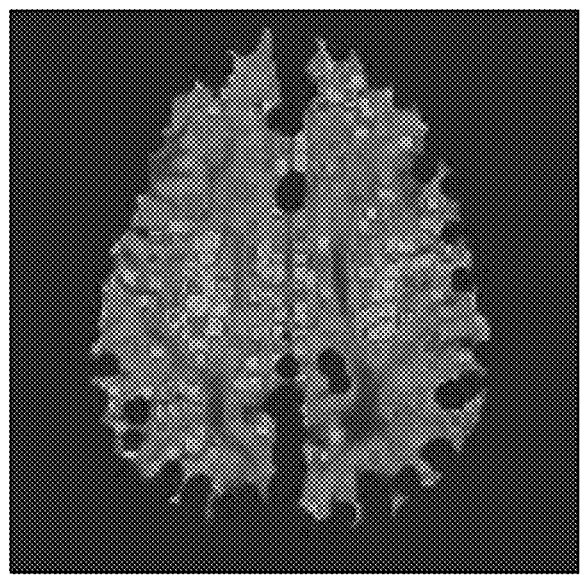

FIG. 7 shows exemplary MRI, PND, and QND brain maps from a diseased individual. The MRI scan shown in FIG. 7 is a diffusion-weighted image that, combined with T1-weighted and T2-weighted images (not shown in FIG. 7), is used to generate a grayscale output image. The grayscale output image serves as the underlying image for the PND and QND maps following removal of the skull and cerebrospinal fluid domains. Red voxels in the PND map represent microstructures that deviate from predicted ranges of structural tolerance for normal tissue. Colored voxels in the QND map similarly represent abnormal voxels, with color added to code for the extent of abnormality (blue=low abnormality, red=high abnormality).

To assess the degenerative state of an individual scan, the abnormality relative coverage (PND), extent of degeneration (QND), estimated total degeneration (END), variation of gray value (gRou), and variation of color value (color roughness, cRou) were further characterized.

Figure 8:
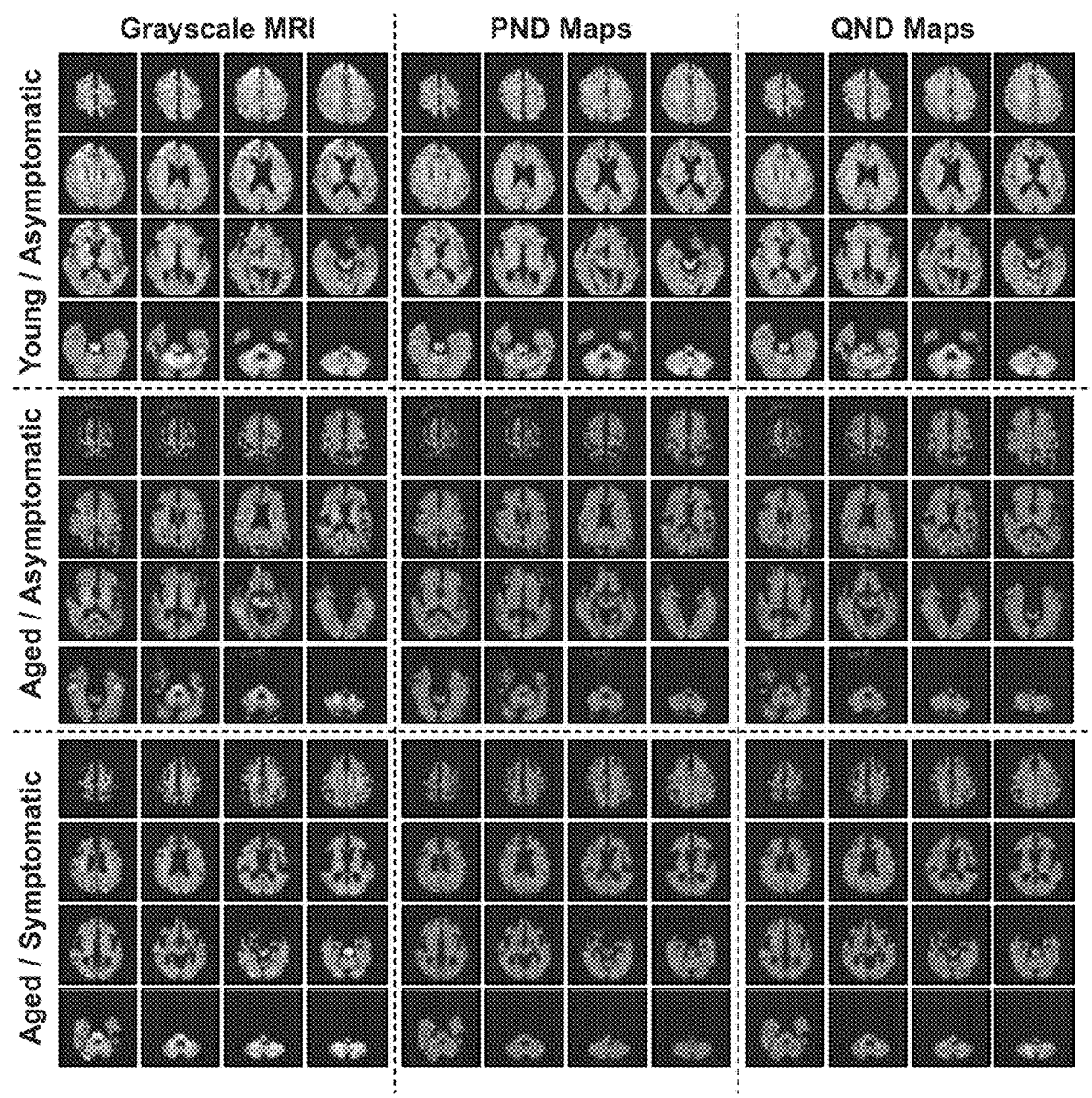
FIG. 8 shows exemplary brain maps for a young, asymptomatic brain, a normal aged brain with no detected neurodegenerative symptoms, and an aged brain with clinical symptoms of severe neurodegeneration.

FIG. 8 shows exemplary brain maps for a young, asymptomatic brain, a normal aged brain with no detected neurodegenerative symptoms, and an aged brain with clinical symptoms of severe degeneration. The grayscale maps reflect determined microstructure at each voxel of each two-dimensional MRI image.

Example 4: Assessment of a Cohort of Subjects

To assess the accuracy of the systems and methods for detecting neurodegeneration described herein, a rigorous microstructure prediction analysis was performed on available MRI data in the Alzheimer's Disease Neuroimaging Initiative (ADNI) database. Scans from healthy individuals and a range of degenerative states, including early and late cognitive impairment and diagnosed AD, were blindly processed using the systems and methods described herein and statistics were generated for each voxel of each image slice. Brain output maps were normalized to 50 slices for approximate region registration. Mean values were calculated for groups segregated by gender, clinical diagnosis, and output parameter (e.g., PND, QND, END, gRou, and cRou shown in FIG. 9). Each essential evaluation parameter was determined across normalized brain regions and with gender segregation. The population was as follows: 152 individuals diagnosed with AD (98 male, 54 female), 507 individuals showing mild cognitive impairment (MCI) (317 male, 190 female), and 206 normal individuals showing no symptoms of cognitive impairment (102 male, 104 female)].

Figure 9:
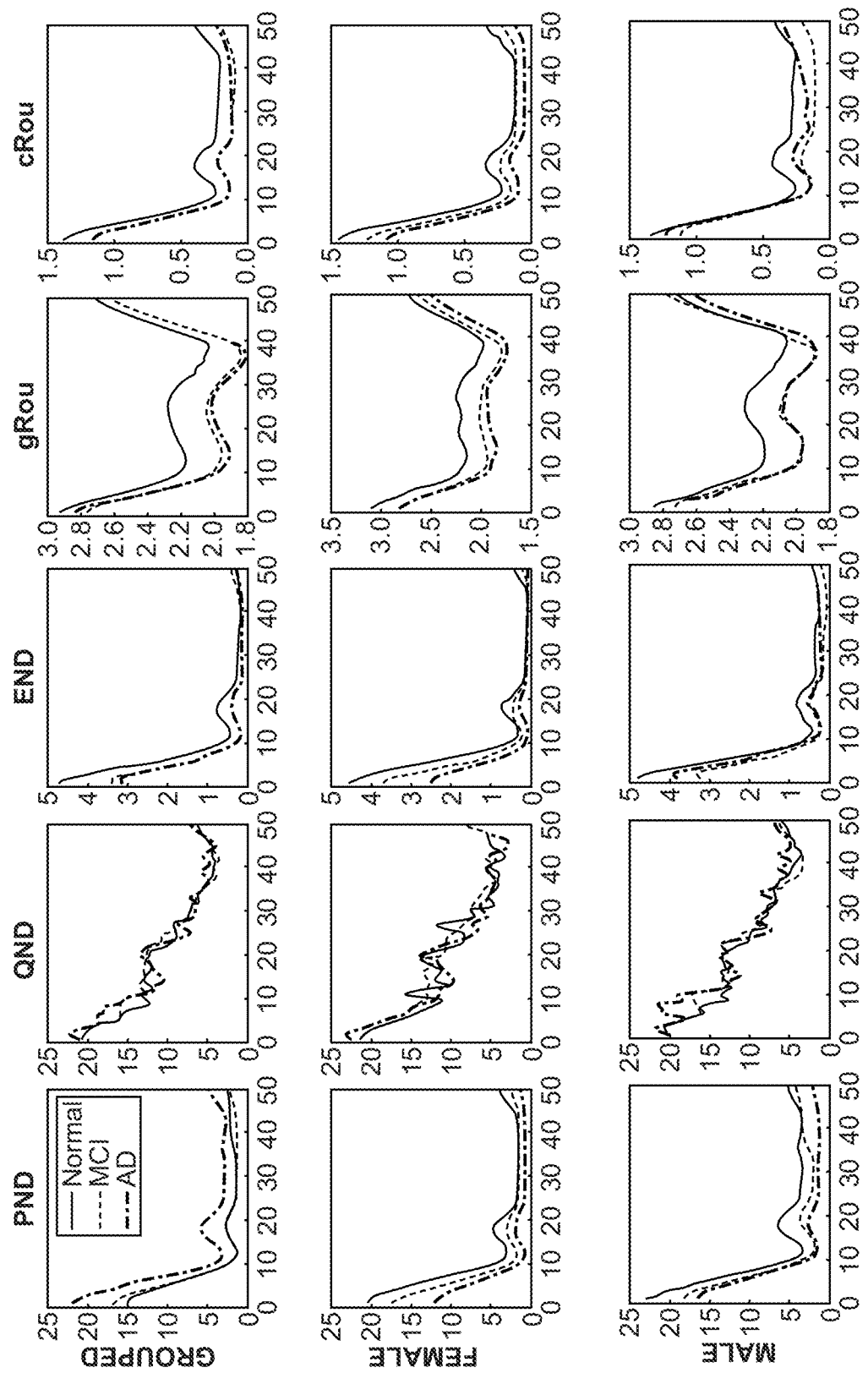
FIG. 9 shows mean plots of degenerative analysis output parameters for Alzheimer's Disease Neuroimaging Initiative (ADNI) images.
Figure 9:
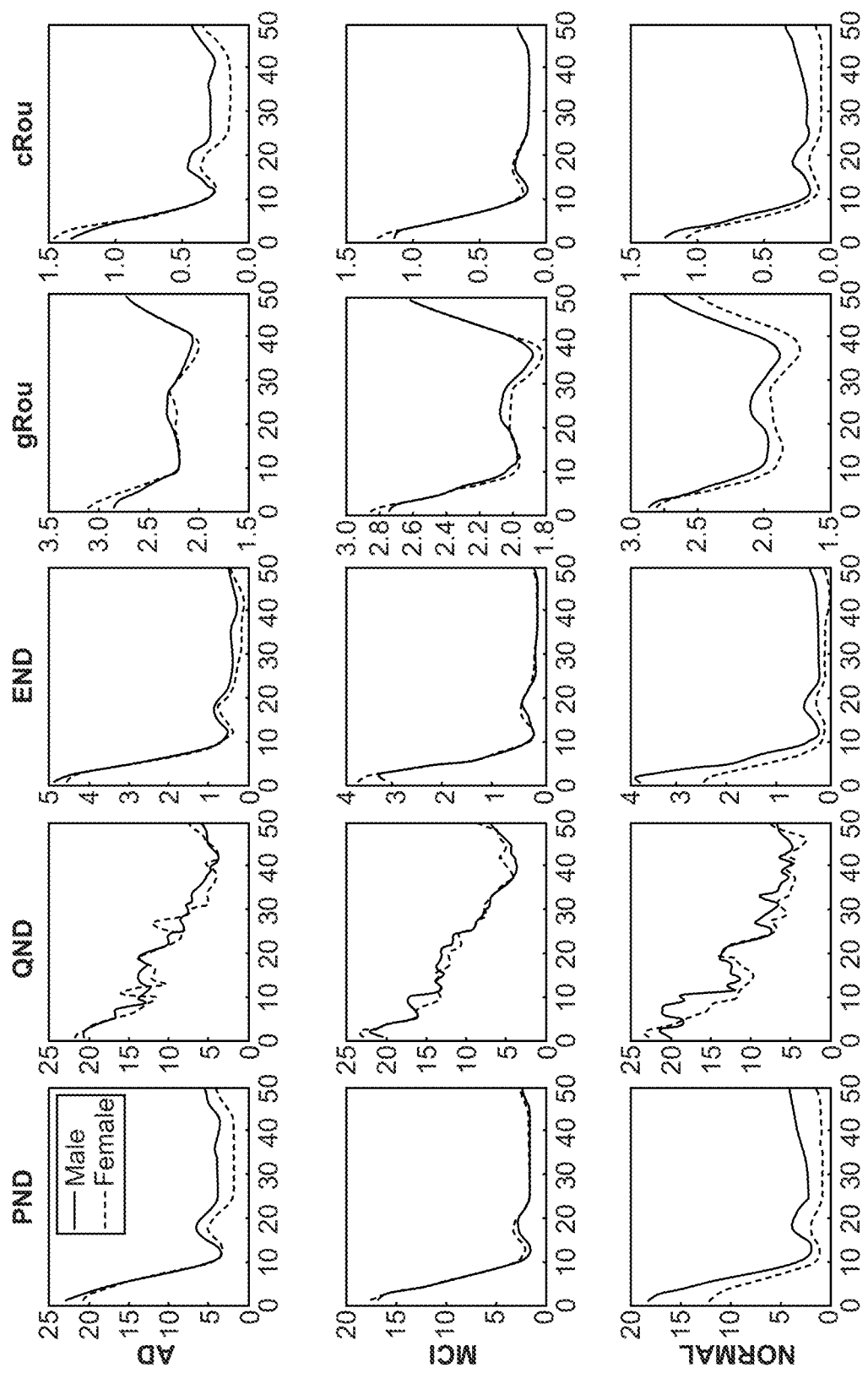

FIG. 9 shows mean plots of degenerative analysis output parameters for the ADNI images. As shown in the mean plots, there is a clear distinction of patients diagnosed with AD within the PND and roughness values across the scan slices, suggesting a robust use in AD diagnosis confirmation. As expected from a mix of early and late impairment stages, the MCI values are shifted toward those of the normal individuals. Considering the estimate that MCI patients progress at a modest rate (10-15% annually) toward full AD, it is striking that the systems and methods described herein can discriminate between MCI and normal patients based on calculated PND and roughness in the female patient scans. These raw data are suggestive of an ability to diagnose some individuals with MCI. The bigger implications, however, are that systems and methods for analyzing brain MRI are providing meaningful estimates of early changes in microstructural state associated with disease.

Example 5: Diagnosis by Machine Learning

With an extensive list of input parameters and output calculations that vary across an anatomically variable image stack, the results can be dramatically improved by applying iterative machine learning on a subset of images. Through machine learning, weighting of known risk factors such as age and gender and less obvious regional patterns of microstructure estimates, the distinguishing power of the degeneration maps can be significantly improved. To validate the diagnostic capacity, the blind ADNI analysis was processed through a BigML algorithm and a predicted diagnosis was assigned to each image set. The resulting data are presented as a confusion matrix in Table 1.

TABLE 1

Confusion matrix

|  |  | Clinical Diagnosis | | |
| --- | --- | --- | --- | --- |
|  |  | Disease | No disease |  |
| Diagnosis by BigML | Disease | 643 | 34 | 0.95 |
|  | No disease | 16 | 172 | 0.91 |
|  |  | 0.98 | 0.83 |  |

The sensitivity or ability to positively detect diseased patients using BigML for categorical prediction (defined here as clinically diagnosed with either MCI or AD) was 98%. The specificity was 93%. The positive predictive value was 95%. The negative predictive value was 91%. Overall accuracy was slightly lower, at 90%, owing to the predicted abnormality in clinically undiagnosed individuals. Whereas some of these individuals may not progress toward a clinical diagnosis, there is a possibility that the systems and methods described herein are detecting structural changes before any cognitive symptoms are present. This population bordering between normal and abnormal is the most difficult yet arguably the most important to address.

Example 6: Longitudinal Brain Imaging Studies

To evaluate the ability to predict early onset of degenerative disease, a collection of MRI scans were acquired from collaborators performing longitudinal brain imaging studies. All patients were imaged at the time of MCI or AD diagnosis (grouped here as Abnormal, though most patients were diagnosed with severe MCI), and most received numerous scans prior to symptom presence and clinical diagnosis. Scans were acquired up to 16 years prior to diagnosis. The cohort distribution and time of scans, relative to diagnosis date, is shown as a bar plot in FIG. 10. Included are a large number of scans from healthy (Normal) individuals with repeated scans over time (in this case, time 0 is the most recent scan and 'years before diagnosis' is years before most recent scan) to reflect the normal individual variation over time.

Figure 10:
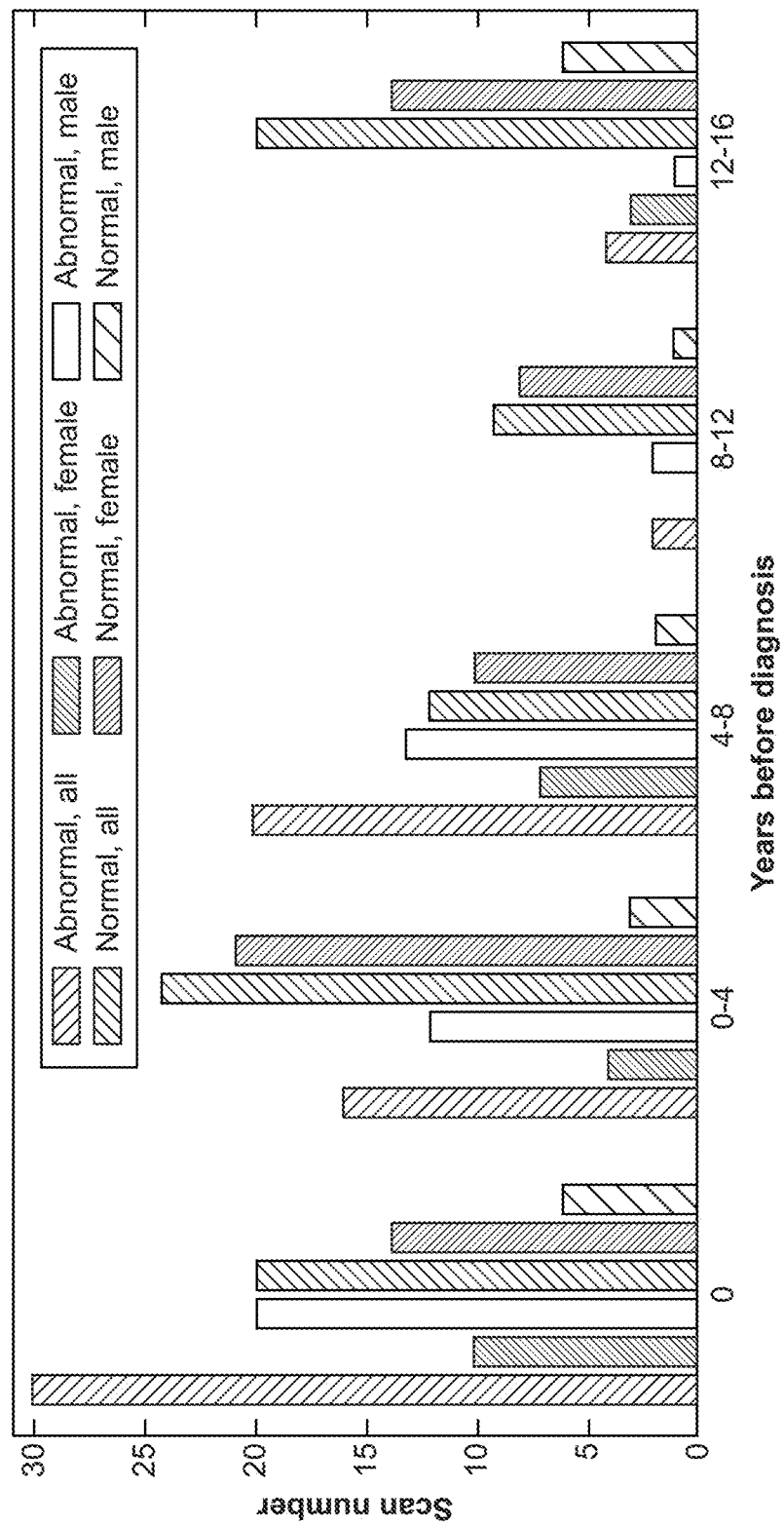
FIG. 10 shows a population distribution for a longitudinal study to evaluate early detection of Alzheimer's disease (AD).

FIG. 10 shows a population distribution for a longitudinal study to evaluate early detection of Alzheimer's disease. Each of the Abnormal patients was diagnosed with either MCI or AD. A majority of abnormal patients were diagnosed with late stage MCI. The scans prior to diagnosis were pooled into 4 year intervals. Segregation by gender shows the population sizes used for the microstructural degeneration analysis. For the Normal individuals, the time point reflects the time before a most recent scan date.

Figure 11:
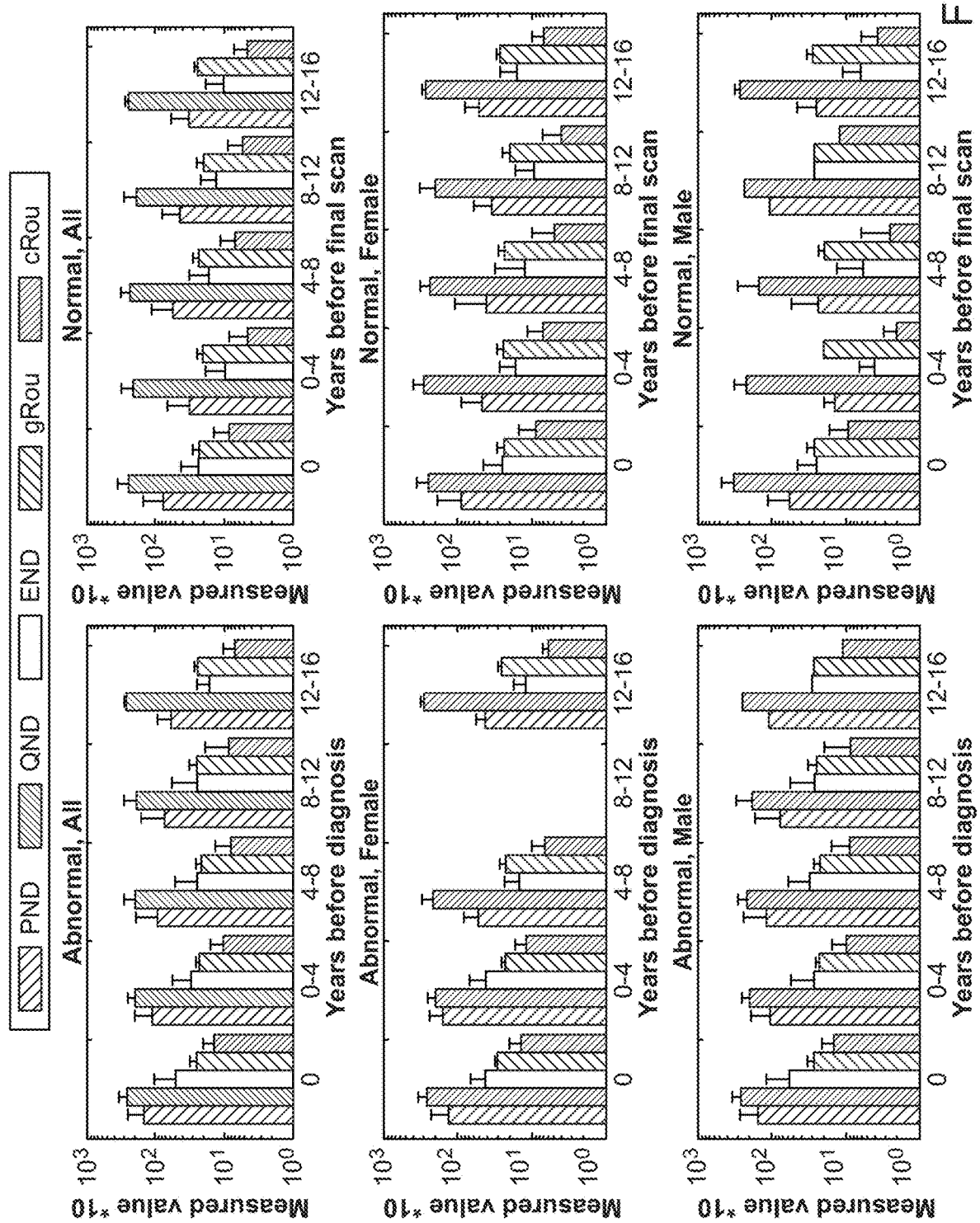
FIG. 11 shows an early detection analysis of MRI images collected longitudinally from the population distribution.

Plots of the principal output values from the degeneration maps show markedly higher PND, END and cRou at the time of diagnosis, as shown in FIG. 11. Most importantly, the raw output values show impressive differentiation of male and female patients relative to normal controls averages, even in the earliest scans. The female cohort shows increased microstructure abnormality at the first time interval before diagnosis, but most of the differentiation is lost at earlier time points, possibly due to a limited sample size or an increasingly lower amounts of, or total absence of, microstructural abnormality in very early time points. Remarkably, the male population PND, QND and END remain elevated above average control values through even the earliest time points. This provides evidence for detection of early degeneration in patients before irreversible degeneration occurs and many years before current practices effectively diagnose the changes.

FIG. 11 shows an early detection analysis of MRI images collected longitudinally from the cohort distribution. Output parameters were blindly generated through microstructure prediction from input MRI scans at each time point. Bars represent mean values and standard deviations for the respective output measure.

Figure 12:
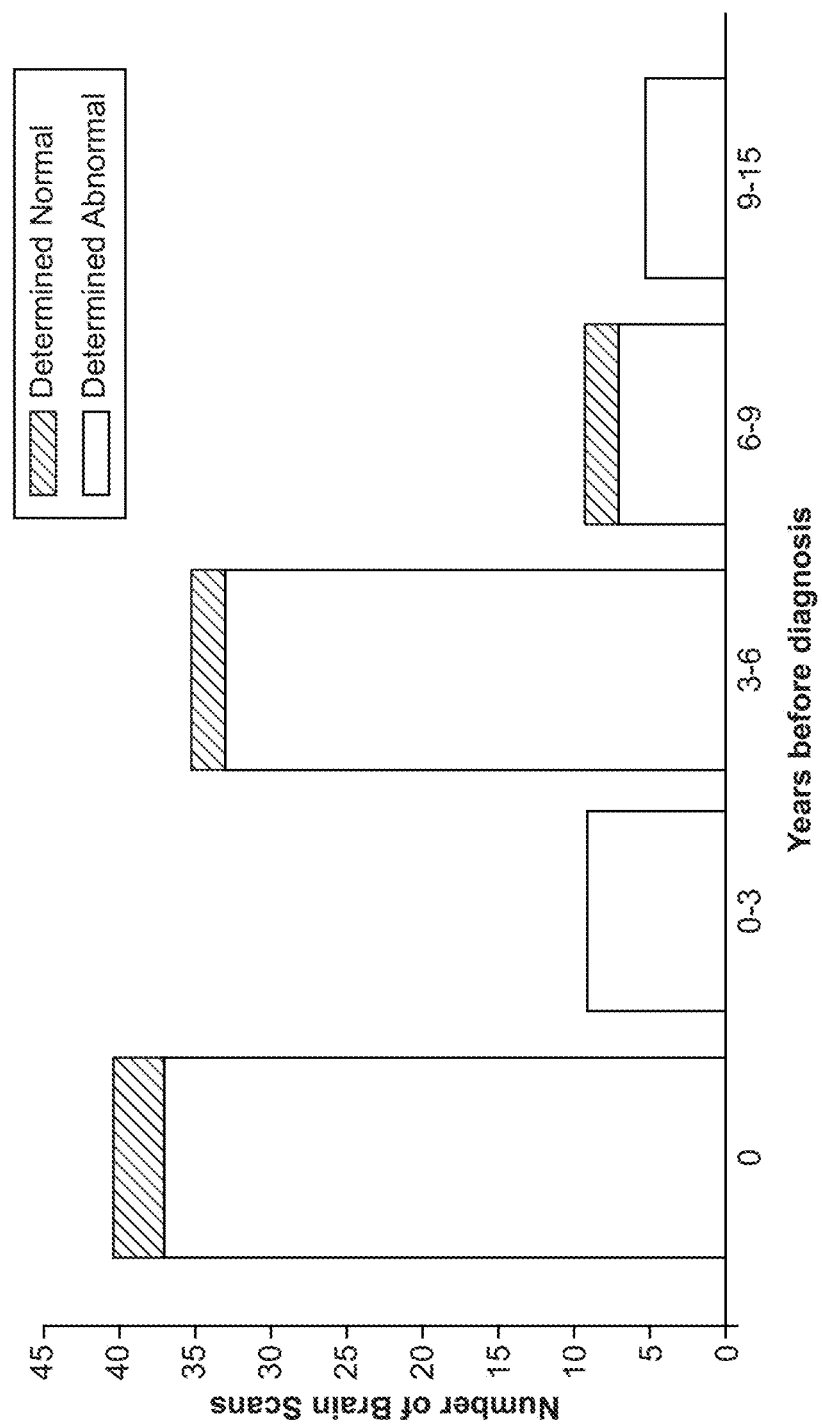
FIG. 12 shows a determination of abnormality in a mixed cohort longitudinal study.

To confirm the early detection ability of our microstructure analysis, output evaluation through BigML processing was repeated using different parameters. After blind processing, each scan was characterized as normal or abnormal and compared to the known clinical diagnoses. Among the 40 diagnosed patients (included here are individuals from the image set without scans prior to diagnosis), a majority was determined to be abnormal, as shown in FIG. 12. From this extended cohort, nearly 93% sensitivity was achieved at the time of diagnosis. Remarkably, a similar 93% sensitivity was achieved throughout all early scans, including multiple scans collected more than a decade before diagnosis, all of which were predicted to be abnormal. Though further detailed evaluation and analysis of newly collected images will be necessary to verify the robustness of our detection system, the initial performance has surpassed current expectations that exist throughout the field of clinical brain imaging. Presented herein is a tool with encouraging performance in detection of early changes in brain tissue structure that can serve as a predictor for future development of degenerative disease. This is a tool desperately needed in the medical community and pharmaceutical industry to aid the detection and prevention of Alzheimer's disease and similar neurodegenerative diseases.

FIG. 12 shows a determination of abnormality in a mixed cohort longitudinal study. All individuals were diagnosed with abnormalities of MCI or AD at time 0. Scans prior to diagnosis were grouped in three-year intervals.

Example 7: Registration of Brain Images

Figure 13:
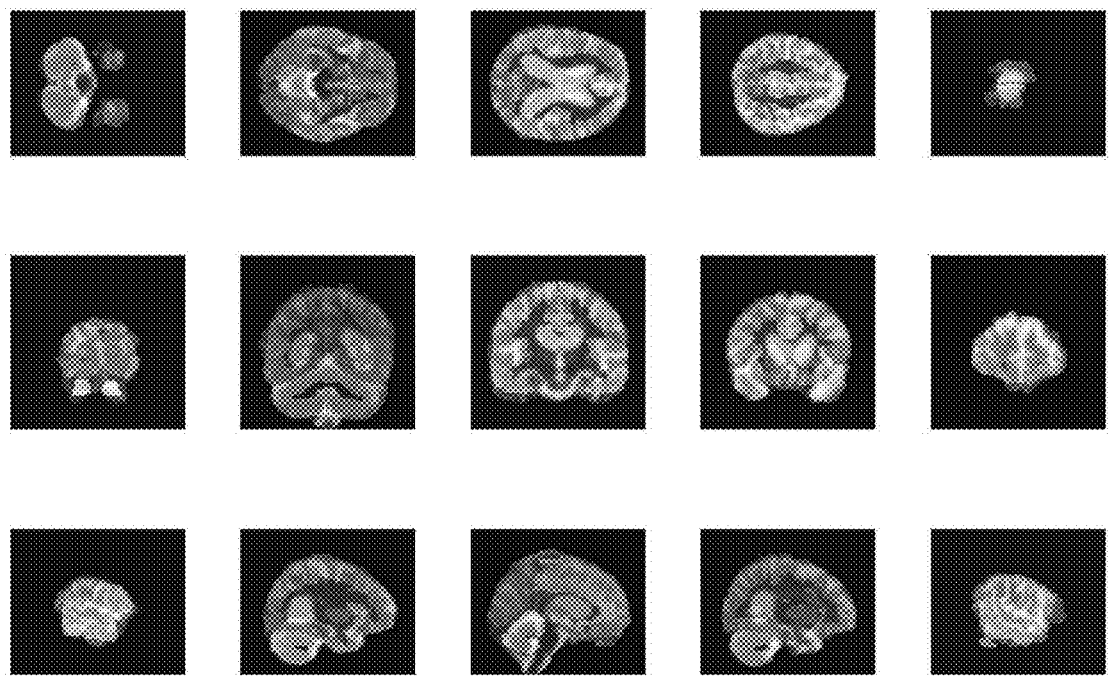
FIG. 13 shows the registration or alignment of subject images to an annotated human brain parcellation atlas.

FIG. 13 shows the registration or alignment of subject images to an annotated human brain parcellation atlas. Each row is a subsample of images throughout the brain from a different imaging axis or orientation.

Example 8: Region-by-Region Diagnosis

Figure 14:
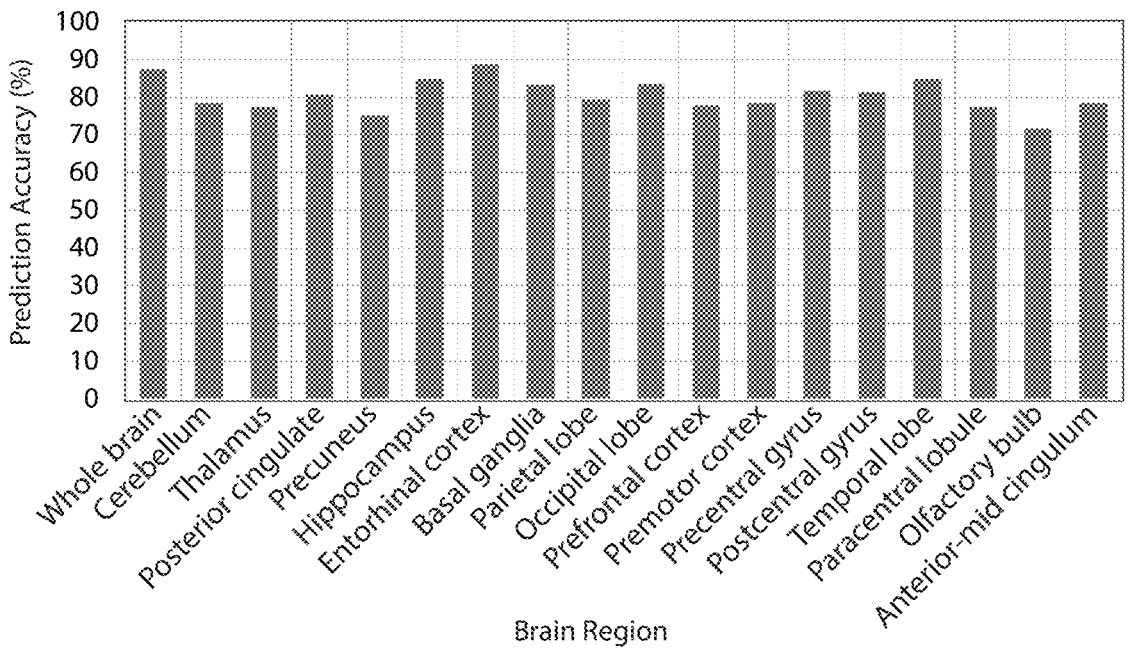
FIG. 14 shows optimized single region prediction accuracy of diagnosis within the ADNI dataset for a variety of brain regions using the systems and methods described herein.

FIG. 14 shows optimized single region prediction accuracy of diagnosis within the ADNI dataset for a variety of brain regions using the systems and methods described herein. Each set of model parameters is tested for optimal prediction accuracy for each independent brain region.

Figure 15:
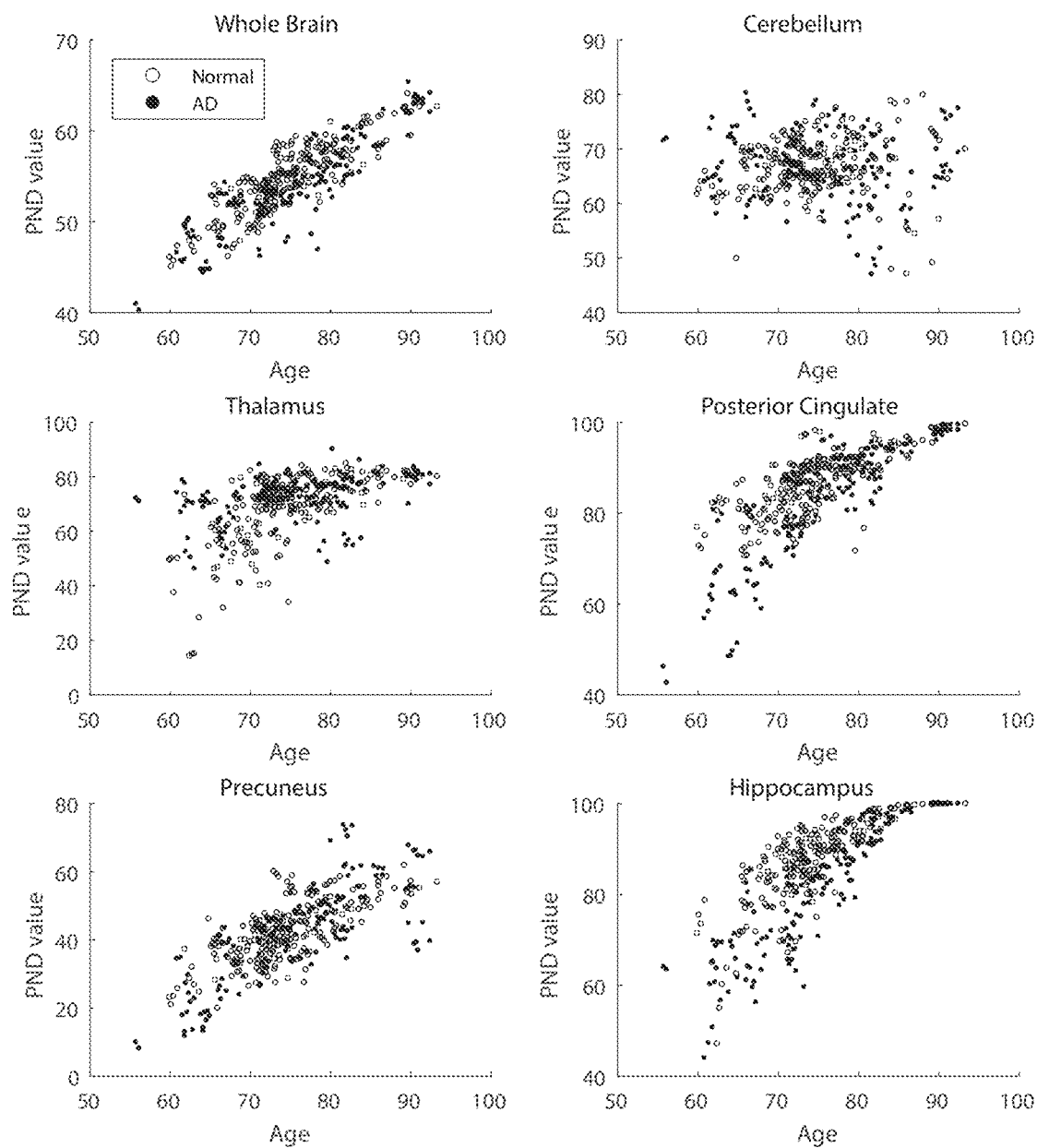
FIG. 15 shows PND measurement distributions across subjects of a variety of ages for the whole brain, cerebellum, thalamus, posterior cingulate, precuneus, and hippocampus.

FIG. 15 shows PND measurement distributions across subjects of a variety of ages for the whole brain, cerebellum, thalamus, posterior cingulate, precuneus, and hippocampus.

Figure 16:
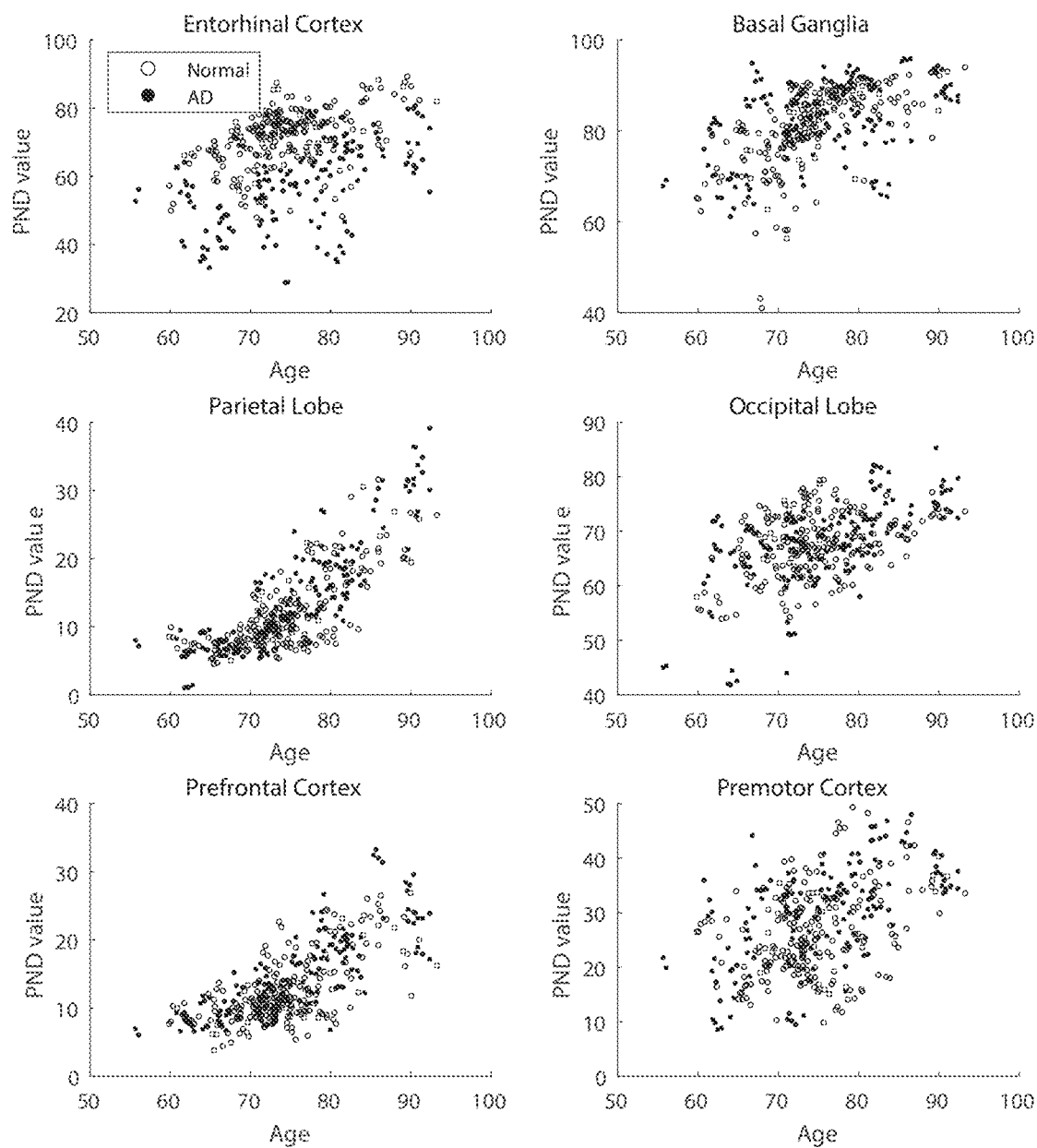
FIG. 16 shows PND measurement distributions across subjects of a variety of ages for the entorhinal cortex, basal ganglia, parietal lobe, occipital lobe, prefrontal cortex, and premotor cortex.

FIG. 16 shows PND measurement distributions across subjects of a variety of ages for the entorhinal cortex, basal ganglia, parietal lobe, occipital lobe, prefrontal cortex, and premotor cortex.

Figure 17:
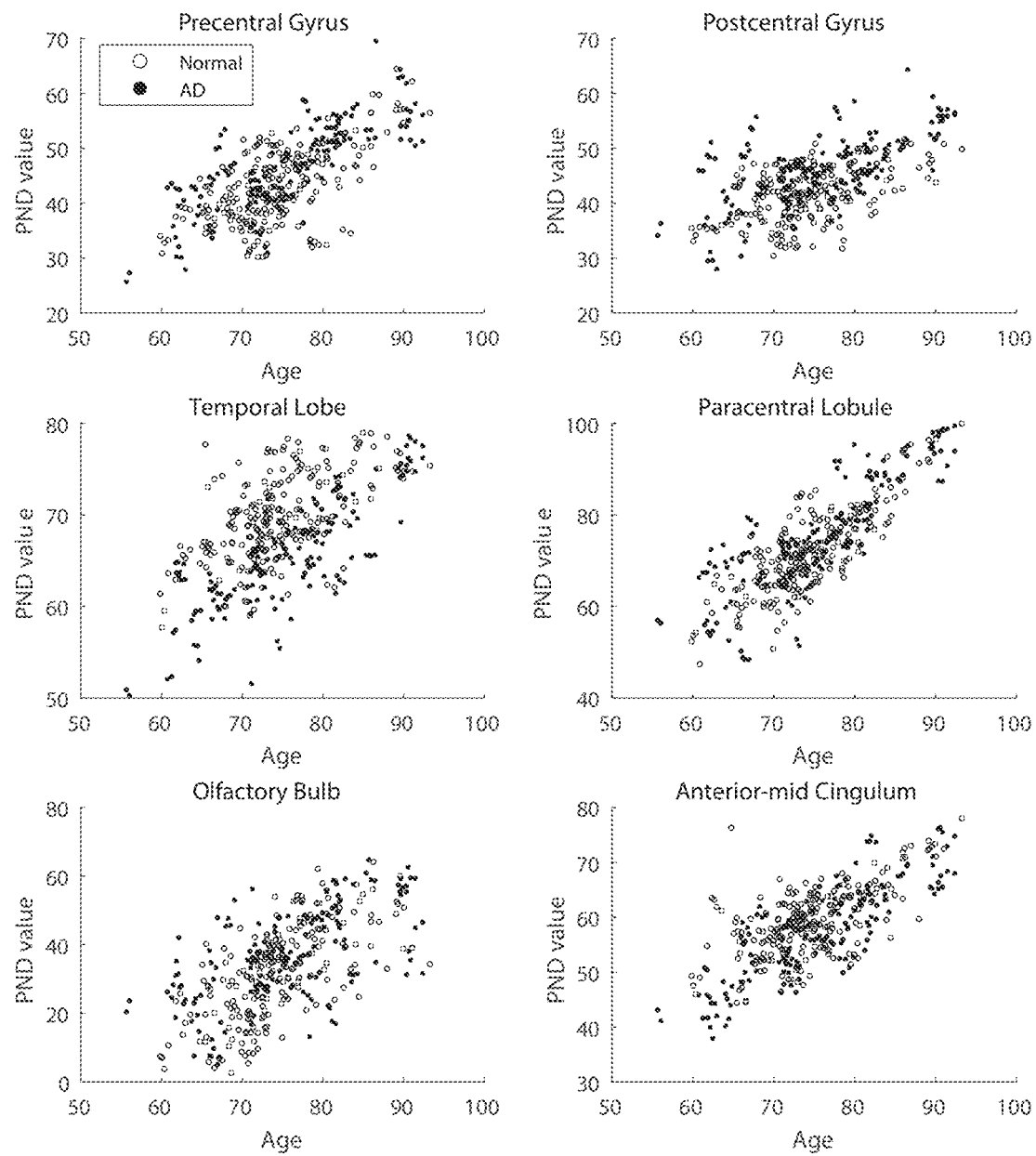
FIG. 17 shows PND measurement distributions across subjects of a variety of ages for the precentral gyrus, postcentral gyrus, temporal lobe, paracentral lobule, olfactory bulb, and anterior-mid cingulum.

FIG. 17 shows PND measurement distributions across subjects of a variety of ages for the precentral gyrus, postcentral gyrus, temporal lobe, paracentral lobule, olfactory bulb, and anterior-mid cingulum.

Example 8: Machine Learning Prediction from Optimized ADNI Image Processing

Figure 18:
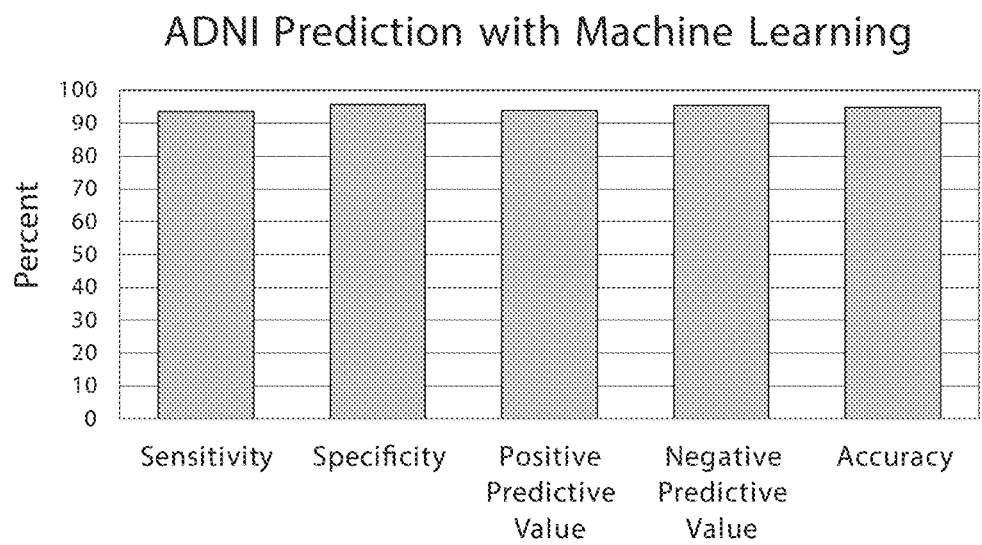
FIG. 18 shows attainable AD diagnostic metrics using machine learning.

FIG. 18 shows attainable AD diagnostic metrics using machine learning. Bootstrap-aggregated decision trees were applied to predict hierarchical classifiers from optimally processed ADNI images.

Example 9: Whole Brain Scoring

Figure 19:
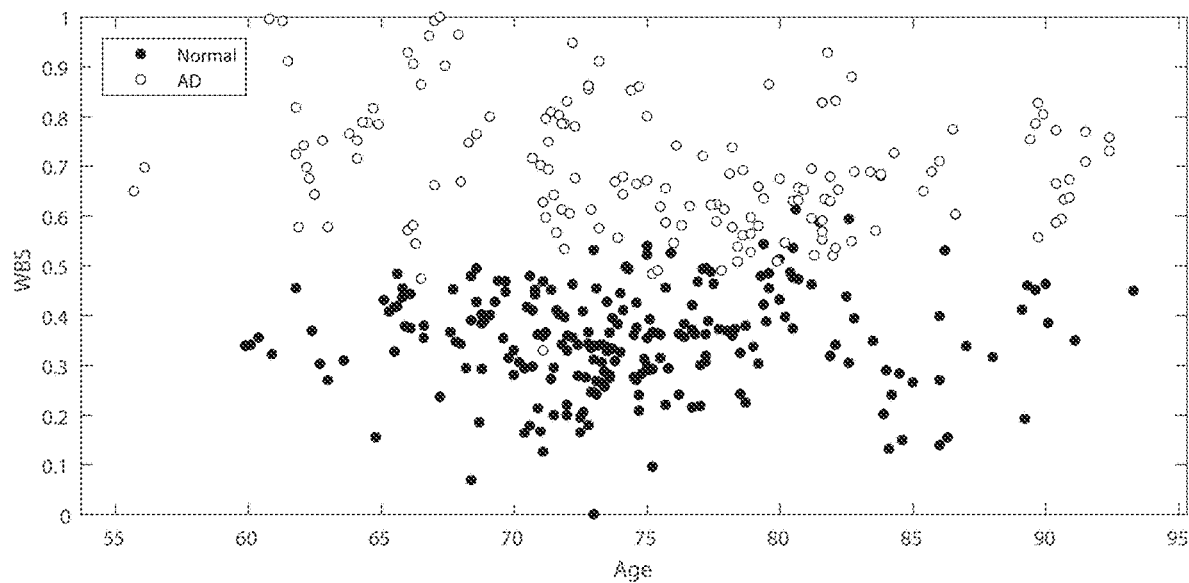
FIG. 19 shows a distribution of whole brain scores (WBS) for ADNI subject scans.

FIG. 19 shows a distribution of whole brain scores (WBS) for ADNI subject scans. The score for each brain was plotted vs the subject's age at the time of scan acquisition. In this example, WBSs were generated through logistic regression analysis of regional PND, QND and END values. The WBS alone provides statistically separated distributions of normal and AD-diagnosed individuals.

Further Aspects of the Disclosure

1. A method for determining a disorder state of brain tissue in a brain of a subject, comprising:

(a) obtaining magnetic resonance imaging (MRI) data comprising at least one MRI image of the brain, the MRI image comprising a plurality of voxels, a voxel of the plurality of voxels being associated with the brain tissue of the brain of the subject and comprising one or more measured MRI parameters in the MRI data;

(b) for the voxel of the plurality of voxels, using one or more computer processors to process the one or more measured MRI parameters with one or more simulated MRI parameters for the voxel, the one or more simulated MRI parameters being generated from one or more microstructural models at the voxel;

(c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and (d) for the voxel of the plurality of voxels, using the diagnostic model to determine the disorder state of the brain tissue associated with the voxel.

2. The method of aspect 1, wherein each voxel comprises a plurality of measured MRI parameters.

3. The method of aspect 1 or 2, wherein the one or more measured MRI parameters are a plurality of measured MRI parameters.

4. The method of any one of aspects 1-3, wherein the one or more simulated MRI parameters are a plurality of simulated MRI parameters.

5. The method of any one of aspects 1-4, further comprising repeating (b)-(d) one or more times for additional voxels of the plurality of voxels.

6. The method of aspect 5, further comprising repeating (b)-(d) for all other voxels of the plurality of voxels.

7. The method of aspect 5, further comprising repeating (b)-(d) for all voxels associated with a specified region of the brain.

8. The method of aspect 5, further comprising repeating (b)-(d) for all voxels associated with an entirety of the brain.

9. The method of aspect 5, further comprising repeating (a)-(d) for a plurality of MRI images, each MRI image of the plurality of MRI images associated with a brain selected from a plurality of brains, each brain of the plurality of brains associated with a subject selected from a plurality of subjects.

10. The method of any one of aspects 1-9, wherein the MRI image is selected from the group consisting of: a longitudinal relaxation time (T1)-weighted MRI image, a transverse relaxation time (T2)-weighted MRI image, and a diffusion-weighted MRI image.

11. The method of any one of aspects 1-10, wherein the measured MRI parameter is selected from the group consisting of: a longitudinal relaxation time (T1), a transverse relaxation time (T2), and a diffusion coefficient.

12. The method of any one of aspects 1-11, wherein the simulated MRI parameter is selected from the group consisting of: a longitudinal relaxation time (T1), a transverse relaxation time (T2), and a diffusion coefficient.

13. The method of any one of aspects 1-12, wherein the one or more microstructural models comprise information regarding a parameter selected from the group consisting of: intracellular content, extracellular content, distribution of extracellular content within interstitial space, distribution of intracellular content within intracellular space, and tissue geometry.

14. The method of any one or aspects 1-13, wherein the one or more microstructural models comprise measured or predicted values of a parameter selected from the group consisting of: cell density, cell shape, cell geometry, cell size, cell distribution, intercellular spacing, extracellular matrix homogeneity, interstitial tortuosity, water to protein ratio, water to lipid ratio, water to carbohydrate ratio, protein to lipid ratio, protein to carbohydrate ratio, and lipid to carbohydrate ratio.

15. The method of any one of aspects 1-14, wherein the one or more microstructural models are selected from a microstructural model library.

16. The method of aspect 15, wherein the microstructural model library comprises at least 100 microstructural models.

17. The method of aspect 15 or 16, wherein the microstructural model library is constructed by:
(a) creating a first microstructural model corresponding to a brain state that is not associated with a disorder; and
(b) iteratively subjecting the first microstructural model to a perturbation, each iteration producing an additional perturbed microstructural model.

18. The method of aspect 17, wherein (b) comprises subjecting the first microstructural model to at least 100 iterations to generate at least 100 perturbed microstructural models.

19. The method of aspect 17 or 18, wherein the first microstructural model is selected based on knowledge of the brain region associated with the voxel.

20. The method of any one of aspects 17-19, wherein the perturbation comprises an operation selected from the group consisting of: depleting cells, altering cellular morphology or distribution, altering intracellular or interstitial physicochemical composition or distribution, altering extracellular matrix composition or distribution, and altering intercellular spacing.

21. The method of any one of aspects 17-20, wherein the perturbation comprises a stochastic procedure.

22. The method of any one of aspects 1-21, wherein the threshold congruence is determined by computing an objective function between the one or more measured MRI parameters and the one or more simulated MRI parameters.

23. The method of aspect 22, wherein the objective function comprises an L1 norm or an L2 norm.

24. The method of any one of aspects 1-23, wherein determining the disorder state of the brain tissue associated with the voxel is achieved at an accuracy of at least 90%.

25. The method of any one of aspects 7-24, wherein determining the disorder state across the brain tissue associated with the specified region of the brain is achieved at an accuracy of at least 90%.

26. The method of any one of aspects 8-25, wherein determining the disorder state of the brain tissue associated with the whole brain of the subject is achieved at an accuracy of at least.

27. The method of any one of aspects 9-26, wherein determining the disorder state of the brain tissue associated the plurality of subjects is achieved at an accuracy of at least 90%.

28. The method of any one of aspects 1-27, wherein the disorder is a non-neurodegenerative disorder.

29. The method of aspect 28, wherein the disorder is selected from the group consisting of: a primary neoplasm, a metastatic neoplasm, a seizure disorder, a seizure disorder with focal cortical dysplasia, a demyelinating disorder, a non-neurodegenerative encephalopathy, a cerebrovascular disease, and a psychological disorder.

30. The method of any one of aspects 1-27, wherein the disorder is a neurodegenerative disorder.

31. The method of aspect 30, wherein the method enables diagnosis of a neurodegenerative disorder more than 5 years prior to the development of symptoms associated with the neurodegenerative disorder.

32. The method of aspect 30 or 31, wherein the method enables monitoring of the neurodegenerative disorder at a plurality of time points, the plurality of time points separated by a plurality of time intervals.

33. The method of any one of aspects 30-32, wherein the neurodegenerative disorder is selected from the group consisting of: Alzheimer's disease, a non-Alzheimer's dementia disorder, Parkinson's disease, a Parkinsonism disorder, a motor neuron disease, Huntington's disease, a Huntington's disease-like syndrome, transmissible spongiform encephalopathy, chronic traumatic encephalopathy, and a tauopathy.

34. The method of any one of aspects 1-33, further comprising constructing a brain map that, for each voxel of the plurality of voxels, indicates the disorder state of the brain tissue associated with the voxel.

35. The method of aspect 34, further comprising displaying the brain map on a graphical user interface of an electronic device of a user.

36. The method of aspect 34 or 35, wherein the brain map comprises a qualitative abnormality map.

37. The method of aspect 34 or 35, wherein the brain map comprises a binary abnormality map.

38. The method of aspect 34 or 35, wherein the brain map comprises a quantitative abnormality map.

39. The method of aspect 34 or 35, wherein the brain map comprises a percent abnormality map.

40. A method for determining a disorder state of a tissue in a portion of a body of a subject, comprising:
- (a) obtaining magnetic resonance imaging (MRI) data comprising at least one MRI image of the tissue, the MRI image comprising a plurality of voxels, a voxel of the plurality of voxels being associated with the tissue of the subject and comprising one or more measured MRI parameters in the MRI data;
- (b) for the voxel of the plurality of voxels, using one or more computer processors to process the one or more measured MRI parameters with one or more simulated MRI parameters for the voxel, the one or more simulated MRI parameters being generated from one or more microstructural models at the voxel;
- (c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and
- (d) for the voxel of the plurality of voxels, using the diagnostic model to determine the disorder state of the tissue associated with the voxel.

41. The method of aspect 38, wherein the tissue is selected from the group consisting of: spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, and non-brain tissue of the head and neck.

42. A non-transitory computer-readable medium comprising machine-executable code that, upon execution by one or more computer processors, implements a method for detecting a disorder state of brain tissue in a brain of a subject, the method comprising:
- (a) obtaining magnetic resonance imaging (MRI) data comprising at least one MRI image of the brain, the MRI image comprising a plurality of voxels, a voxel of the plurality of voxels being associated with the brain tissue of the brain of the subject and comprising one or more measured MRI parameters in the MRI data;
- (b) for the voxel of the plurality of voxels, using one or more computer processors to process the one or more measured MRI parameters with one or more simulated MRI parameters for the voxel, the one or more simulated MRI parameters being generated from one or more microstructural models at the voxel;
- (c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and
- (d) for the voxel of the plurality of voxels, using the diagnostic model to determine the disorder state of the brain tissue associated with the voxel.

43. The non-transitory computer-readable medium of aspect 42, wherein each voxel comprises a plurality of measured MRI parameters.

44. The non-transitory computer-readable medium of aspect 42 or 43, wherein the one or more measured MRI parameters are a plurality of measured MRI parameters.

45. The non-transitory computer-readable medium of any one of aspects 42-44, wherein the one or more simulated MRI parameters are a plurality of simulated MRI parameters.

46. The non-transitory computer-readable medium of any one of aspects 42-45, wherein the method further comprises repeating (b)-(d) one or more times for additional voxels of the plurality of voxels.

47. The non-transitory computer-readable medium of aspect 46, wherein the method further comprises repeating (b)-(d) for all other voxels of the plurality of voxels.

48. The non-transitory computer-readable medium of aspect 46, wherein the method further comprises repeating (b)-(d) for all voxels associated with a specified region of the brain.

49. The non-transitory computer-readable medium of aspect 46, wherein the method further comprises repeating (b)-(d) for all voxels associated with an entirety of the brain.

50. The non-transitory computer-readable medium of aspect 46, wherein the method further comprises repeating (a)-(d) for a plurality of MRI images, each MRI image of the plurality of MRI images associated with a brain selected from a plurality of brains, each brain of the plurality of brains associated with a subject selected from a plurality of subjects.

51. The non-transitory computer-readable medium of any one of aspects 42-50, wherein the MRI image is selected from the group consisting of: a longitudinal relaxation time (T1)-weighted MRI image, a transverse relaxation time (T2)-weighted MRI image, and a diffusion-weighted MRI image.

52. The non-transitory computer-readable medium of any one of aspects 42-51, wherein the measured MRI parameter is selected from the group consisting of: a longitudinal relaxation time (T1), a transverse relaxation time (T2), and a diffusion coefficient.

53. The non-transitory computer-readable medium of any one of aspects 42-52, wherein the simulated MRI parameter is selected from the group consisting of: a longitudinal relaxation time (T1), a transverse relaxation time (T2), and a diffusion coefficient.

54. The non-transitory computer-readable medium of any one of aspects 42-53, wherein the one or more microstructural models comprise information regarding a parameter selected from the group consisting of: intracellular content, extracellular content, distribution of extracellular content within interstitial space, distribution of intracellular content within intracellular space, and tissue geometry.

55. The non-transitory computer-readable medium of any one or aspects 42-54, wherein the one or more microstructural models comprise measured or predicted values of a parameter selected from the group consisting of: cell density, cell shape, cell geometry, cell size, cell distribution, intercellular spacing, extracellular matrix homogeneity, interstitial tortuosity, water to protein ratio, water to lipid ratio, water to carbohydrate ratio, protein to lipid ratio, protein to carbohydrate ratio, and lipid to carbohydrate ratio.

56. The non-transitory computer-readable medium of any one of aspects 42-55, wherein the one or more microstructural models are selected from a microstructural model library.

57. The non-transitory computer-readable medium of aspect 56, wherein the microstructural model library comprises at least 100 microstructural models.

58. The non-transitory computer-readable medium of aspect 56 or 57, wherein the microstructural model library is constructed by:
  (a) creating a first microstructural model corresponding to a brain state that is not associated with a disorder; and
  (b) iteratively subjecting the first microstructural model to a perturbation, each iteration producing an additional perturbed microstructural model.

59. The non-transitory computer-readable medium of aspect 58, wherein (b) comprises subjecting the first microstructural model to at least 100 iterations to generate at least 100 perturbed microstructural models.

60. The non-transitory computer-readable medium of aspect 58 or 59, wherein the first microstructural model is selected based on knowledge of the brain region associated with the voxel.

61. The non-transitory computer-readable medium of any one of aspects 58-60, wherein the perturbation comprises an operation selected from the group consisting of: depleting cells, altering cellular morphology or distribution, altering intracellular or interstitial physico-chemical composition or distribution, altering extracellular matrix composition or distribution, and altering intercellular spacing.

62. The non-transitory computer-readable medium of any one of aspects 58-61, wherein the perturbation comprises a stochastic procedure.

63. The non-transitory computer-readable medium of any one of aspects 42-62, wherein the threshold congruence is determined by computing an objective function between the one or more measured MRI parameters and the one or more simulated MRI parameters.

64. The non-transitory computer-readable medium of aspect 63, wherein the objective function comprises an L1 norm or an L2 norm.

65. The non-transitory computer-readable medium of any one of aspects 42-64, wherein determining the disorder state of the brain tissue associated with the voxel is achieved at an accuracy of at least 90%.

66. The non-transitory computer-readable medium of any one of aspects 48-65, wherein determining the disorder state across the brain tissue associated with the specified region of the brain is achieved at an accuracy of at least 90%.

67. The non-transitory computer-readable medium of any one of aspects 49-66, wherein determining the disorder state of the brain tissue associated with the whole brain of the subject is achieved at an accuracy of at least 90%.

68. The non-transitory computer-readable medium of any one of aspects 50-67, wherein determining the disorder state of the brain tissue associated the plurality of subjects is achieved at an accuracy of at least 90%.

69. The non-transitory computer-readable medium of any one of aspects 42-68, wherein the disorder is a non-neurodegenerative disorder.

70. The non-transitory computer-readable medium of aspect 69, wherein the disorder is selected from the group consisting of: a primary neoplasm, a metastatic neoplasm, a seizure disorder, a seizure disorder with focal cortical dysplasia, a demyelinating disorder, a non-neurodegenerative encephalopathy, a cerebrovascular disease, and a psychological disorder.

71. The non-transitory computer-readable medium of any one of aspects 42-68, wherein the disorder is a neurodegenerative disorder.

72. The non-transitory computer-readable medium of aspect 71, wherein the method enables diagnosis of a neurodegenerative disorder more than 5 years prior to the development of symptoms associated with the neurodegenerative disorder.

73. The non-transitory computer-readable medium of aspect 71 or 72, wherein the method enables monitoring of the neurodegenerative disorder at a plurality of time points, the plurality of time points separated by a plurality of time intervals.

74. The non-transitory computer-readable medium of any one of aspects 71-73, wherein the neurodegenerative disorder is selected from the group consisting of: Alzheimer's disease, a non-Alzheimer's dementia disorder, Parkinson's disease, a Parkinsonism disorder, a motor neuron disease, Huntington's disease, a Huntington's disease-like syndrome, a transmissible spongiform encephalopathy, chronic traumatic encephalopathy, and a tauopathy.

75. The non-transitory computer-readable medium of any one of aspects 42-74, wherein the method further comprises constructing a brain map that, for each voxel of the plurality of voxels, indicates the disorder state of the brain tissue associated with the voxel.

76. The non-transitory computer-readable medium of aspect 75, wherein the method further comprises displaying the brain map on a graphical user interface of an electronic device of a user.

77. The non-transitory computer-readable medium of aspect 75 or 76, wherein the brain map comprises a qualitative abnormality map.

78. The non-transitory computer-readable medium of aspect 75 or 76, wherein the brain map comprises a binary abnormality map.

79. The non-transitory computer-readable medium of aspect 75 or 76, wherein the brain map comprises a quantitative abnormality map.

80. The non-transitory computer-readable medium of aspect 75 or 76, wherein the brain map comprises a percent abnormality map.

81. A non-transitory computer-readable medium comprising machine-executable code that, upon execution by one or more computer processors, implements a method for detecting a disorder state of a tissue of a subject, the method comprising:

(a) obtaining magnetic resonance imaging (MRI) data comprising at least one MRI image of the tissue, the MRI image comprising a plurality of voxels, a voxel of the plurality of voxels being associated with the tissue of the subject and comprising one or more measured MRI parameters in the MRI data;

(b) for the voxel of the plurality of voxels, using one or more computer processors to process the one or more measured MRI parameters with one or more simulated MRI parameters for the voxel, the one or more simulated MRI parameters being generated from one or more microstructural models at the voxel;

(c) for the voxel of the plurality of voxels, selecting a diagnostic model from the one or more microstructural models, the diagnostic model meeting a threshold congruence between the one or more measured MRI parameters and the one or more simulated MRI parameters associated with the diagnostic model; and (d) for the voxel of the plurality of voxels, using the diagnostic model to determine the disorder state of the tissue associated with the voxel.

82. The non-transitory computer-readable medium of aspect 82, wherein the tissue is selected from the group consisting of: spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, and non-brain tissue of the head and neck.

83. A system for determining a disorder state of brain tissue in a brain of a subject, comprising:
(a) a database comprising magnetic resonance imaging (MRI) data comprising at least one MRI image of the brain, the MRI image comprising a plurality of voxels, a voxel of the plurality of voxels being associated with the brain tissue of the brain of the subject and comprising a measured MRI parameter in the MRI data; and
(b) one or more computer processors operatively coupled to the database, wherein the one or more computer processors are individually or collectively programmed to:
  i. for the voxel of the plurality of voxels, use one or more computer processors to process the one or more measured MRI parameters with one or more simulated MRI parameters for the voxel, the one or more simulated MRI parameters being generated from one or more microstructural models at the voxel;
  ii. for the voxel of the plurality of voxels, select a diagnostic model from the one or more microstructural models, the diagnostic model meeting a threshold congruence between the one or more measured MRI parameters and the one or more simulated MRI parameters associated with the diagnostic model; and
  iii. for the voxel of the plurality of voxels, use the diagnostic model to determine the disorder state of the brain tissue associated with the voxel.

84. The system of aspect 83, wherein each voxel comprises a plurality of measured MRI parameters.

85. The system of aspect 83 or 84, wherein the one or more measured MRI parameters are a plurality of measured MRI parameters.

86. The system of any one of aspects 83-85, wherein the one or more simulated MRI parameters are a plurality of simulated MRI parameters.

87. The system of any one of aspects 83-86, wherein the one or more computer processors are further individually or collectively programmed to repeat (b)-(d) one or more times for additional voxels of the plurality of voxels.

88. The system of aspect 87, wherein the one or more computer processors are further individually or collectively programmed to repeat (b)-(d) for all other voxels of the plurality of voxels.

89. The system of aspect 87, wherein the one or more computer processors are further individually or collectively programmed to repeat (b)-(d) for all voxels associated with a specified region of the brain.

90. The system of aspect 87, wherein the one or more computer processors are further individually or collectively programmed to repeat (b)-(d) for all voxels associated with an entirety of the brain.

91. The system of aspect 87, wherein the one or more computer processors are further individually or collectively programmed to repeat (a)-(d) for a plurality of MRI images, each MRI image of the plurality of MRI images associated with a brain selected from a plurality of brains, each brain of the plurality of brains associated with a subject selected from a plurality of subjects.

92. The system of any one of aspects 83-91, wherein the MRI image is selected from the group consisting of: a longitudinal relaxation time (T1)-weighted MRI image, a transverse relaxation time (T2)-weighted MRI image, and a diffusion-weighted MRI image.

93. The system of any one of aspects 83-92, wherein the measured MRI parameter is selected from the group consisting of: a longitudinal relaxation time (T1), a transverse relaxation time (T2), and a diffusion coefficient.

94. The system of any one of aspects 83-93, wherein the simulated MRI parameter is selected from the group consisting of: a longitudinal relaxation time (T1), a transverse relaxation time (T2), and a diffusion coefficient.

95. The system of any one of aspects 83-94, wherein the one or more microstructural models comprise information regarding a parameter selected from the group consisting of: intracellular content, extracellular content, distribution of extracellular content within interstitial space, distribution of intracellular content within intracellular space, and tissue geometry.

96. The system of any one or aspects 83-95, wherein the one or more microstructural models comprise measured or predicted values of a parameter selected from the group consisting of: cell density, cell shape, cell geometry, cell size, cell distribution, intercellular spacing, extracellular matrix homogeneity, interstitial tortuosity, water to protein ratio, water to lipid ratio, water to carbohydrate ratio, protein to lipid ratio, protein to carbohydrate ratio, and lipid to carbohydrate ratio.

97. The system of any one of aspects 83-96, wherein the one or more microstructural models are selected from a microstructural model library.

98. The system of aspect 97, wherein the microstructural model library comprises at least 100 microstructural models.

99. The system of aspect 97 or 98, wherein the microstructural model library is constructed by:
(a) creating a first microstructural model corresponding to a brain state that is not associated with a disorder; and
(b) iteratively subjecting the first microstructural model to a perturbation, each iteration producing an additional perturbed microstructural model.

100. The system of aspect 99, wherein (b) comprises subjecting the first microstructural model to at least 100 iterations to generate at least 100 perturbed microstructural models.

101. The system of aspect 99 or 100, wherein the first microstructural model is selected based on knowledge of the brain region associated with the voxel.

102. The system of any one of aspects 99-101, wherein the perturbation comprises an operation selected from the group consisting of: depleting cells, altering cellular morphology or distribution, altering intracellular or interstitial physico-chemical composition or distribution, altering extracellular matrix composition or distribution, and altering intercellular spacing.

103. The system of any one of aspects 99-102, wherein the perturbation comprises a stochastic procedure.

104. The system of any one of aspects 83-103, wherein the threshold congruence is determined by computing an objective function between the one or more measured MRI parameters and the one or more simulated MRI parameters.

105. The system of aspect 104, wherein the objective function comprises an L1 norm or an L2 norm.

106. The system of any one of aspects 83-105, wherein determining the disorder state of the brain tissue associated with the voxel is achieved at an accuracy of at least 90%.

107. The system of any one of aspects 89-106, wherein determining the disorder state across the brain tissue associated with the specified region of the brain is achieved at an accuracy of at least 90%.

108. The system of any one of aspects 90-107, wherein determining the disorder state of the brain tissue associated with the whole brain of the subject is achieved at an accuracy of at least 90%.

109. The system of any one of aspects 91-108, wherein determining the disorder state of the brain tissue associated the plurality of subjects is achieved at an accuracy of at least 90%.

110. The system of any one of aspects 83-109, wherein the disorder is a non-neurodegenerative disorder.

111. The system of aspect 110, wherein the disorder is selected from the group consisting of: a primary neoplasm, a metastatic neoplasm, a seizure disorder, a seizure disorder with focal cortical dysplasia, a demyelinating disorder, a non-neurodegenerative encephalopathy, a cerebrovascular disorder, and a psychological disorder.

112. The system of any one of aspects 83-111, wherein the disorder is a neurodegenerative disorder.

113. The system of aspect 112, wherein the system enables diagnosis of a neurodegenerative disorder more than 5 years prior to the development of symptoms associated with the neurodegenerative disorder.

114. The system of aspect 112 or 113, wherein the system enables monitoring of the neurodegenerative disorder at a plurality of time points, the plurality of time points separated by a plurality of time intervals.

115. The system any one of aspects 112-114, wherein the neurodegenerative disorder is selected from the group consisting of: Alzheimer's disease, a non-Alzheimer's dementia disorder, Parkinson's disease, a Parkinsonism disorder, a motor neuron disease, Huntington's disease, a Huntington's disease-like syndrome, a transmissible spongiform encephalopathy, chronic traumatic encephalopathy, and a tauopathy.

116. The system of any one of aspects 83-115, wherein the one or more computer processors are further individually or collectively programmed to construct a brain map that, for each voxel of the plurality of voxels, indicates the disorder state of the brain tissue associated with the voxel.

117. The system of aspect 116, wherein the one or more computer processors are further individually or collectively programmed to display the brain map on a graphical user interface of an electronic device of a user.

118. The system of aspect 116 or 117, wherein the brain map comprises a qualitative abnormality map.

119. The system of aspect 116 or 117, wherein the brain map comprises a binary abnormality map.

120. The system of aspect 116 or 117, wherein the brain map comprises a quantitative abnormality map.

121. The system of aspect 116 or 117, wherein the brain map comprises a percent abnormality map.

122. A system for determining a disorder state of a tissue in a portion of a body of a subject, comprising:
  (a) a database comprising magnetic resonance imaging (MRI) data comprising at least one MRI image of the brain, the MRI image comprising a plurality of voxels, a voxel of the plurality of voxels being associated with the brain tissue of the brain of the subject and comprising a measured MRI parameter in the MRI data; and
  (b) one or more computer processors operatively coupled to the database, wherein the one or more computer processors are individually or collectively programmed to:
    i. for the voxel of the plurality of voxels, use one or more computer processors to process the one or more measured MRI parameters with one or more simulated MRI parameters for the voxel, the one or more simulated MRI parameters being generated from one or more microstructural models at the voxel;
    ii. for the voxel of the plurality of voxels, select a diagnostic model from the one or more microstructural models, the diagnostic model meeting a threshold congruence between the one or more measured MRI parameters and the one or more simulated MRI parameters associated with the diagnostic model; and
    iii. for the voxel of the plurality of voxels, use the diagnostic model to determine the disorder state of the tissue associated with the voxel.

123. The system of aspect 122, wherein the tissue is selected from the group consisting of: spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, and non-brain tissue of the head and neck.

What is claimed is:

1. A computer-implemented method for determining a disorder state of brain tissue in a brain of a subject, comprising:
  (a) obtaining magnetic resonance imaging (MRI) data comprising at least one MRI image of the brain, the MRI image comprising a plurality of voxels, a voxel of the plurality of voxels being associated with the brain tissue of the brain of the subject and comprising one or more measured Mill parameters in the MRI data;
  (b) for the voxel of the plurality of voxels, using one or more computer processors to process the one or more measured Mill parameters with one or more simulated Mill parameters for the voxel, the one or more simulated Mill parameters being generated from one or more microstructural models at the voxel, wherein the one or more microstructural models comprise predicted values of at least one parameter from at least one machine learning procedure, wherein the at least one parameter is selected from the group consisting of: cell density, cell shape, cell geometry, cell size, cell distribution, intercellular spacing, extracellular matrix composition, extracellular matrix distribution, extracellular matrix homogeneity, and interstitial tortuosity within the voxel, which one or more microstructural models are not generated from the Mill data;

(c) for the voxel of the plurality of voxels, selecting a diagnostic model from the one or more microstructural models, the diagnostic model meeting a threshold congruence between the one or more measured MRI parameters and the one or more simulated Mill parameters associated with the diagnostic model; and (d) using the diagnostic model to generate an output indicative of the disorder state of the brain tissue associated with at least the voxel.

2. The method of claim 1, wherein the one or more measured MRI parameters are a plurality of measured MRI parameters.

3. The method of claim 2, wherein the one or more simulated MRI parameters are a plurality of simulated MRI parameters.

4. The method of claim 1, further comprising repeating (b)-(d) for all other voxels of the plurality of voxels.

5. The method of claim 1, further comprising repeating (b)-(d) for all voxels associated with a specified region of the brain to determine disorder states across the brain tissue associated with the specified region of the brain of the subject.

6. The method of claim 5, wherein determining the disorder states across the brain tissue associated with the specified region of the brain is achieved at an accuracy of at least 90%.

7. The method of claim 1, further comprising repeating (b)-(d) for all voxels associated with an entirety of the brain to determine disorder states of the brain tissue associated with the entirety of the brain of the subject.

8. The method of claim 7, wherein determining the disorder states of the brain tissue associated with the entirety of the brain of the subject is achieved at an accuracy of at least 90%.

9. The method of claim 1, further comprising repeating (a)-(d) for a plurality of MRI images, each MRI image of the plurality of MRI images associated with a brain selected from a plurality of brains, each brain of the plurality of brains associated with a subject selected from a plurality of subjects, to determine disorder states of the brain tissue associated with the plurality of subjects.

10. The method of claim 9, wherein determining the disorder states of the brain tissue associated with the plurality of subjects is achieved at an accuracy of at least 90%.

11. The method of claim 1, wherein the MRI image is selected from the group consisting of: a longitudinal relaxation time (T1)-weighted MRI image, a transverse relaxation time (T2)-weighted MRI image, and a diffusion-weighted MRI image.

12. The method of claim 11, wherein the one or more measured MRI parameters are selected from the group consisting of: a longitudinal relaxation time (T1), a transverse relaxation time (T2), and a diffusion coefficient.

13. The method of claim 1, wherein the one or more microstructural models comprise information regarding at least one parameter selected from the group consisting of: intracellular content, extracellular content, distribution of extracellular content within interstitial space, distribution of intracellular content within intracellular space, and tissue geometry.

14. The method of claim 1, wherein the one or more microstructural models are selected from a microstructural model library.

15. The method of claim 14, wherein the microstructural model library is constructed by:
(a) creating a first microstructural model corresponding to a brain state that is not associated with a disorder; and
(b) iteratively subjecting the first microstructural model to a perturbation, each iteration producing an additional perturbed microstructural model.

16. The method of claim 15, wherein the perturbation comprises an operation selected from the group consisting of: depleting cells, altering cellular morphology or distribution, altering intracellular or interstitial physico-chemical composition or distribution, altering extracellular matrix composition or distribution, and altering intercellular spacing.

17. The method of claim 16, wherein the perturbation comprises a stochastic procedure.

18. The method of claim 17, wherein the threshold congruence is determined by computing an objective function between the one or more measured MRI parameters and the one or more simulated MRI parameters.

19. The method of claim 18, wherein the objective function comprises an L1 norm or an L2 norm.

20. The method of claim 1, wherein determining the disorder state of the brain tissue associated with the voxel is achieved at an accuracy of at least 90%.

21. The method of claim 1, wherein the disorder is a non-neurodegenerative disorder.

22. The method of claim 21, wherein the disorder is selected from the group consisting of: a primary neoplasm, a metastatic neoplasm, a motor neuron disease, a seizure disorder, a seizure disorder with focal cortical dysplasia, multiple sclerosis, a non-neurodegenerative encephalopathy, and a psychological disorder.

23. The method of claim 1, wherein the disorder is a neurodegenerative disorder.

24. The method of claim 23, wherein the method enables diagnosis of a neurodegenerative disorder more than 5 years prior to the development of symptoms associated with the neurodegenerative disorder.

25. The method of claim 23, wherein the method enables monitoring of the neurodegenerative disorder at a plurality of time points, the plurality of time points separated by a plurality of time intervals.

26. The method of claim 23, wherein the neurodegenerative disorder is selected from the group consisting of: Alzheimer's disease, a non-Alzheimer's dementia disorder, Parkinson's disease, a Parkinsonism disorder, a motor neuron disease, Huntington's disease, a Huntington's disease-like syndrome, transmissible spongiform encephalopathy, chronic traumatic encephalopathy, and a tauopathy.

27. The method of claim 1, further comprising constructing a brain map that, for each voxel of the plurality of voxels, indicates the disorder state of the brain tissue associated with the voxel.

28. The method of claim 27, further comprising displaying the brain map on a graphical user interface of an electronic device of a user.

29. The method of claim 27, wherein the brain map is selected from the group consisting of: a qualitative abnormality map, a binary abnormality map, a quantitative abnormality map, and a percent abnormality map.

30. The method of claim 1, further comprising, prior to (b), using the at least one machine learning procedure to generate the predicted values of the at least one parameter.

* * * * *

UNITED STATES PATENT AND TRADEMARK OFFICE
CERTIFICATE OF CORRECTION

Page 1 of 2

PATENT NO. : 10,573,414 B2
APPLICATION NO. : 15/987794
DATED : February 25, 2020
INVENTOR(S) : Padideh Kamali-Zare et al.

It is certified that error appears in the above-identified patent and that said Letters Patent is hereby corrected as shown below:

In the Claims

Column 44; Line 60; Claim 1 please delete:
"more measured Mill parameters in the MRI data;"
And replace with:
"more measured MRI parameters in the MRI data;"

Column 44; Line 63; Claim 1 please delete:
"measured Mill parameters with one or more simulated"
And replace with:
"measured MRI parameters with one or more simulated"

Column 44; Line 64; Claim 1 please delete:
"Mill parameters for the voxel, the one or more simu-"
And replace with:
"MRI parameters for the voxel, the one or more simu-"

Column 44; Line 65; Claim 1 please delete:
"lated Mill parameters being generated from one or"
And replace with:
"lated MRI parameters being generated from one or"

Column 45; Line 9; Claim 1 please delete:
"are not generated from the Mill data;"
And replace with:
"are not generated from the MRI data;"

Column 45; Line 14; Claim 1 please delete:
"parameters and the one or more simulated Mill param-"
And replace with:

Signed and Sealed this
Twenty-ninth Day of September, 2020

Andrei Iancu
*Director of the United States Patent and Trademark Office*

CERTIFICATE OF CORRECTION (continued)

"parameters and the one or more simulated MRI param-"

Column 46; Line 32-33; Claim 21 please delete:
"The method of claim 1, wherein the disorder is a non-neurodegenerative disorder."
And replace with:
"The method of claim 1, wherein the disorder state is associated with a non-neurodegenerative disorder."

Column 46; Line 34-35; Claim 22 please delete:
"The method of claim 21, wherein the disorder is selected from the group consisting of: a primary neoplasm,"
And replace with:
"The method of claim 21, wherein the non-neurodegenerative disorder is selected from the group consisting of: a primary neoplasm,"

Column 46; Lines 40-41; Claim 23 please delete:
"The method of claim 1, wherein the disorder is a neurodegenerative disorder."
And replace with:
"The method of claim 1, wherein the disorder state is associated with a neurodegenerative disorder."

Column 46; Line 43; Claim 24 please delete:
"diagnosis of a neurodegenerative disorder more than 5 years"
And replace with:
"identification of the neurodegenerative disorder more than 5 years"